(12) United States Patent
Carpenter et al.

(10) Patent No.: US 7,864,322 B2
(45) Date of Patent: Jan. 4, 2011

(54) OPTICAL METHODS AND SYSTEMS FOR DETECTING A CONSTITUENT IN A GAS CONTAINING OXYGEN IN HARSH ENVIRONMENTS

(75) Inventors: Michael A. Carpenter, Scotia, NY (US); George Sirinakis, Bronx, NY (US)

(73) Assignee: The Research Foundation of State University of New York, Albany, NY (US)

( * ) Notice: Subject to any disclaimer, the term of this patent is extended or adjusted under 35 U.S.C. 154(b) by 331 days.

(21) Appl. No.: 12/293,501

(22) PCT Filed: Mar. 22, 2007

(86) PCT No.: PCT/US2007/064665

§ 371 (c)(1),
(2), (4) Date: Sep. 18, 2008

(87) PCT Pub. No.: WO2007/121032

PCT Pub. Date: Oct. 25, 2007

(65) Prior Publication Data

US 2009/0207413 A1 Aug. 20, 2009

Related U.S. Application Data

(60) Provisional application No. 60/785,025, filed on Mar. 23, 2006.

(51) Int. Cl.
*G01N 21/00* (2006.01)
(52) U.S. Cl. .................. 356/437; 250/343; 436/134
(58) Field of Classification Search ......... 356/432–440, 356/445–448; 250/343; 436/134, 167; 422/88, 422/91, 94
See application file for complete search history.

(56) References Cited

U.S. PATENT DOCUMENTS 4,030,340 A    6/1977   Chang .......................... 73/23

(Continued)

FOREIGN PATENT DOCUMENTS

WO    WO 03/084869    10/2003

(Continued)

OTHER PUBLICATIONS

Carpenter et al., The International Search Report for WO/2007/121032 (PCT 2007/064665), 4 pages, application published Oct. 25, 2007.

(Continued)

*Primary Examiner*—Hoa Q Pham
(74) *Attorney, Agent, or Firm*—Heslin Rothenberg Farley & Mesiti P.C.

(57) ABSTRACT

A method for detecting a gas phase constituent such as carbon monoxide, nitrogen dioxide, hydrogen, or hydrocarbons in a gas comprising oxygen such as air, includes providing a sensing material or film having a metal embedded in a catalytically active matrix such as gold embedded in a yttria stabilized zirconia (YSZ) matrix. The method may include annealing the sensing material at about 900° C., exposing the sensing material and gas to a temperature above 400° C., projecting light onto the sensing material, and detecting a change in the absorption spectrum of the sensing material due to the exposure of the sensing material to the gas in air at the temperature which causes a chemical reaction in the sensing material compared to the absorption spectrum of the sensing material in the absence of the gas. Systems employing such a method are also disclosed.

42 Claims, 24 Drawing Sheets

U.S. PATENT DOCUMENTS

| | | | |
|---|---|---|---|
| 4,358,951 A | 11/1982 | Chang | 73/23 |
| 4,668,635 A | 5/1987 | Forster | 436/134 |
| 4,927,766 A * | 5/1990 | Auerbach et al. | 436/44 |
| 5,229,833 A | 7/1993 | Stewart | 356/364 |
| 5,327,225 A | 7/1994 | Bender et al. | 356/445 |
| 5,405,583 A | 4/1995 | Goswami et al. | 422/86 |
| 5,770,326 A | 6/1998 | Limaye | 429/30 |
| 5,841,021 A | 11/1998 | De Castro et al. | 73/23.2 |
| 5,905,000 A | 5/1999 | Yadav et al. | 429/33 |
| 5,942,676 A | 8/1999 | Potthast et al. | 73/31.06 |
| 5,958,340 A | 9/1999 | Meyer et al. | 422/90 |
| 5,958,361 A | 9/1999 | Laime et al. | 423/592 |
| 6,149,868 A | 11/2000 | Natan et al. | 422/82.05 |
| 6,160,278 A | 12/2000 | Liu et al. | 257/252 |
| 6,200,445 B1 | 3/2001 | Yokota et al. | 204/424 |
| 6,202,471 B1 | 3/2001 | Yadav et al. | 73/31.05 |
| 6,254,749 B1 | 7/2001 | Yokota et al. | 204/424 |
| 6,293,137 B1 | 9/2001 | Liu et al. | 73/31.06 |
| 6,330,062 B1 | 12/2001 | Corn et al. | 356/445 |
| 6,344,271 B1 | 2/2002 | Yadav et al. | 428/402 |
| 6,387,560 B1 | 5/2002 | Yadav et al. | 429/45 |
| 6,466,323 B1 | 10/2002 | Anderson et al. | 356/445 |
| 6,480,282 B1 | 11/2002 | Chinowsky et al. | 356/445 |
| 6,513,362 B1 | 2/2003 | Yadav et al. | 73/31.05 |
| 6,515,749 B2 | 2/2003 | Pipino | 356/440 |
| 6,537,498 B1 | 3/2003 | Lewis | 422/82.01 |
| 6,557,393 B1 | 5/2003 | Gokhfeld et al. | 73/23.31 |
| 6,596,236 B2 | 7/2003 | DiMeo, Jr. et al. | 422/88 |
| 6,617,049 B2 | 9/2003 | Darolia et al. | 428/633 |
| 6,620,525 B1 | 9/2003 | Rigney et al. | 428/633 |
| 6,635,162 B2 | 10/2003 | Sugaya et al. | 204/426 |
| 6,689,266 B2 | 2/2004 | Kato et al. | 204/425 |
| 6,691,554 B2 | 2/2004 | Eastman et al. | 73/25.03 |
| 6,705,152 B2 | 3/2004 | Routkevitch et al. | 73/31.05 |
| 2002/0017126 A1 | 2/2002 | DiMeo et al. | 73/23.2 |
| 2002/0118027 A1 | 8/2002 | Routkevitch | 324/694 |
| 2002/0122971 A1 | 9/2002 | Ghosh et al. | 429/40 |
| 2002/0177143 A1 | 11/2002 | Mirkin et al. | 435/6 |
| 2002/0184939 A1 | 12/2002 | Yadav et al. | 73/24.04 |
| 2002/0190251 A1 | 12/2002 | Kunitake et al. | 438/85 |
| 2003/0026961 A1 | 2/2003 | De La Preta et al. | 428/209 |
| 2003/0027327 A1 | 2/2003 | Cunningham et al. | 435/6 |
| 2003/0034486 A1 | 2/2003 | Korgel et al. | 257/E33.04 |
| 2003/0056570 A1 | 3/2003 | Shin et al. | 73/25.05 |
| 2003/0079999 A1 | 5/2003 | Penner et al. | 204/400 |
| 2003/0106795 A1 | 6/2003 | Katafuchi et al. | 204/424 |
| 2003/0111341 A1 | 6/2003 | Wiedenmann et al. | 204/290.01 |
| 2003/0117691 A1 | 6/2003 | Bi et al. | 359/333 |
| 2003/0121780 A1 | 7/2003 | Dutta et al. | 204/424 |
| 2003/0129608 A1 | 7/2003 | Mirkin et al. | 425/6 |
| 2003/0143581 A1 | 7/2003 | Franzen et al. | 435/6 |
| 2003/0152863 A1 | 8/2003 | Prieta et al. | 430/270.1 |
| 2003/0153088 A1 | 8/2003 | DiMeo, Jr. et al. | 436/113 |
| 2003/0159927 A1 | 8/2003 | Lewis et al. | 204/403.14 |
| 2003/0174384 A1 | 9/2003 | Halas et al. | 359/296 |
| 2003/0178571 A1 | 9/2003 | Nayfeh et al. | 427/58 |
| 2003/0205078 A1 | 11/2003 | Hasei et al. | 73/23.31 |
| 2003/0219753 A1 | 11/2003 | Quinn et al. | 435/6 |
| 2003/0219822 A1 | 11/2003 | Quinn et al. | 427/2.11 |
| 2004/0000479 A1 | 1/2004 | Katafuchi et al. | 204/424 |
| 2004/0005485 A1 | 1/2004 | Yadav et al. | 429/122 |
| 2004/0023428 A1 | 2/2004 | Gole et al. | 438/48 |
| 2004/0038106 A1 | 2/2004 | Saito et al. | 429/33 |
| 2004/0038255 A1 | 2/2004 | Mirkin et al. | 435/6 |
| 2004/0043272 A1 | 3/2004 | Gorte et al. | 429/33 |
| 2004/0063215 A1 | 4/2004 | Horiuchi et al. | 436/121 |
| 2005/0089260 A1 | 4/2005 | Mechery et al. | |

FOREIGN PATENT DOCUMENTS

WO    WO 2007/121032    10/2007

OTHER PUBLICATIONS

Carpenter et al., International Preliminary Report on Patentability for WO 2007/121032 (PCT/2007/064665), 9 pages, application published Oct. 25, 2007.

Ando et al., Optical and Electrical $H_2$- and $NO_2$-Sensing Properties of $Au/In_XO_YN_Z$ Films, IEEE Sensors Journal, vol. 04, No. 2, 5 pages, Apr. 2004.

Ando et al., Optical CO Sensitivity of AU-CuO Composite Film by Use of the Plasmon Absorption Change, Sensors and Acutators, vol. B., No. 9, pp. 589-595, 2003.

Englebienne et al., High-Throughput Screening Using the Surface Plasmon Resonance Effect of Colloidal Gold Particles, Analyst, vol. 126, pp. 1645-1651, Sep. 2001.

Kreibig et al., Optical Properties of Metal Clusters, Springer, New York, pp. 96-99 and 294-302, 1995.

* cited by examiner

OPTICAL METHODS AND SYSTEMS FOR DETECTING A CONSTITUENT IN A GAS CONTAINING OXYGEN IN HARSH ENVIRONMENTS

PRIORITY INFORMATION

This application is a national stage filing under Section 371 of International Application No. PCT/US2007/064665, filed on Mar. 22, 2007 and published in English on Oct. 25, 2007, as WO 2007/121032, which is a continuation of and claims priority from pending U.S. Provisional Application No. 60/785,025 filed on Mar. 23, 2006, entitled "Optical Methods Using Au-YSZ Nanocomposites For Detecting A Gas In Harsh Environments", the entire subject matter of these applications being incorporated herein by reference.

GOVERNMENT RIGHTS

This invention was made with Government support under contract number DE-FG26-04NT42184 awarded by the United States Department of Energy. The Government has certain rights in the invention.

FIELD OF THE INVENTION

This invention relates generally to sensors, and more specifically to high temperature compatible optical gas sensors.

BACKGROUND OF THE INVENTION

Environmental concerns associated with the use of fossil fuels have stimulated efforts towards developing various gas sensors. Although existing sensing technologies based on solid electrolytes, oxide semiconductors, and field effect devices exhibit significant potential for sensing applications at intermediate temperatures, e.g., below 600° C., there are challenges associated with poor device stability and low selectivity. Moreover, these challenges are more apparent at temperatures above 600° C.

An alternative approach to gas sensing includes optical methods such as absorption spectroscopy. Optical sensing techniques are immune to electromagnetic noise, and inherently safer than their electrical counterpart since the sensing elements are isolated from the interrogating electronics, thus minimizing the danger of explosion in environments with flammable or explosive gases.

Experimental effort has been focused on the development of sensors that employ noble metal nanoparticles due to their unique optical properties. In particular, gold (Au) and silver (Ag) nanoparticles exhibit a strong surface plasmon resonance (SPR) band whose shape and spectral position is not only highly dependent on the refractive index of the host medium but also on chemical interactions, e.g. catalytic reactions at the interface between the metal and the surrounding environment. Theoretical modeling of silver nanoparticles surrounded by a CO matrix/medium at room temperature has been undertaken. Kreibig, U.; Vollmer, M.; *Optical Properties of Metal Clusters*; Springer, N.Y., 1995.

Recently, Haruta and coworkers demonstrated the sensing potential of Au nanoparticles dispersed in a copper oxide (CuO) matrix to carbon monoxide (CO), at concentrations ranging from 50 to 10,000 ppm (1 vol. %) in air up between 175° C. and 300° C. Ando, M.; Kobayashi, T.; Iijima, S.; Haruta, M. *Optical CO Sensitivity of Au—CuO Composite Film by Use of the Plasmon Absorption Chang*, Sensors and Actuators B-CHEMICAL 2003, Vol. 96, Iss. 3, pp 589-595.

The sensing mechanism was related to changes in the refractive index of the matrix due to the partial reduction of the CuO grains upon exposure to CO.

The inventors of the present invention earlier studied the effect of annealing temperatures on the microstructure and optical properties of $Y_2O_3$-stabilized $ZrO_2$—Au nanocomposite films which were presented at the Materials Research Society meeting in Sep. 2004. FIG. 1 displays x-ray diffraction (XRD) patterns for the evolution of the microstructure of Au—YSZ nanocomposite films as a function of annealing temperature. The XRD patterns are plotted as diffraction peak intensity versus diffraction angle $2\theta$ for the range from 25° C. to 55° C. As can be seen in FIG. 1, two poly crystalline phases were detected, one corresponding to the tetragonal YSZ phase, and the other to the face centered cubic Au phase. In addition, the XRD peaks became sharper and more intense with higher annealing temperature, indicating an increase in the crystallinity, and hence a rise in the average size of both the YSZ and the Au crystallites. These trends are attributed to the availability of a larger thermal energy at higher annealing temperature to drive crystallite coalescence, growth, and realignment.

The average Au crystallite size was calculated from the Scherrer formula using the Au XRD (111) reflection. The results of this analysis are displayed in FIG. 2, which plots the average crystallite size for Au as a function of annealing temperature. FIG. 2 indicates that the average Au crystallite size exhibited a gradual rise with annealing temperature, from about 4.0 nanometers (nm) at 600° C. to about 8.0 nm at 800° C. to about 9.5 nm at 900° C. However, a marked increase of about 5.5 nm was observed as the annealing temperature was increased from about 900° C. to about 1000° C., indicating a potential change in the underlying mechanism that drives the coalescence and regrowth of the Au crystallites.

FIG. 3 displays RBS data for the spatial distribution of Au atoms versus film depth within the YSZ matrix. The data are plotted as elemental RBS peak intensity versus RBS channel, with the width and the height of each peak determined by the spatial distribution and relative concentration of the corresponding element, respectively. In this context, no significant change was observed in the height or FWHM of the Au RBS peak with respect to the Zr peak as a function of annealing temperature, indicating that the average concentration of Au atoms as a function of film depth is not affected by the annealing process.

These findings, when coupled to the increase described above in the average Au crystallite size with the rise in annealing temperature, imply that at temperatures below about 900° C., Au crystallites grow through a solid state diffusion mechanism of individual Au atoms through the YSZ matrix. Alternatively, above about 900° C., the annealing temperature approaches the melting point of Au. The latter is 1064° C. for bulk Au but has been shown to be significantly lower for Au in nanoparticle form. For instance, a melting point of about 900° C. has been reported for 10 nm silica-encapsulated Au particles.

Accordingly, it is believed that above about 900° C., the growth of Au crystallites is still governed by the diffusion of Au atoms through the YSZ matrix. However, in contrast to solid-state diffusion of individual Au atoms observed below about 900° C., the marked increase in Au crystallite size above 900° C. suggests the occurrence of Au crystallite growth via an Ostwald ripening process. In this process, larger Au crystallites with lower interfacial curvature grow at the expense of their smaller counterparts with higher interfacial curvature, via the migration of individual Au atoms. This suggestion is in agreement with previous studies on the growth mechanism of Au nanoparticles in a silica matrix.

With regard to the film optical properties (at room temperature and in air) as a function of annealing temperature, FIG. 4 illustrates a typical absorbance spectra of Au—YSZ nanocomposite films over the wavelength region from about 300 nm to about 800 nm. As can be seen in FIG. 4, an SPR band due to the light-induced collective, oscillatory motion of the conduction electrons of Au is prominently present around about 600 nm. The band maximum was observed to shift toward longer wavelengths or "redshift" and become sharper and more intense with higher annealing temperature.

There is a need for further optical gas sensors that can operate under harsh environments and at high temperatures.

SUMMARY OF THE INVENTION

In a first aspect, the present invention provides a method for detecting a constituent in a gas containing oxygen. The method includes providing a sensing material comprising a metal embedded in a catalytically active matrix, exposing the sensing material and the constituent in the gas to a temperature above about 400° C., projecting light onto the sensing material, and detecting the constituent in the gas by a change in the absorption spectrum of the sensing material due to the exposure of the sensing material to the constituent in the gas at the temperature which causes a chemical reaction in the sensing material compared to the absorption spectrum of the sensing material in the absence of the constituent in the gas.

In a second aspect, the present invention provides a method for detecting a plurality of constituents in a gas containing oxygen. The method includes providing a plurality of sensing materials comprising a metal embedded in a catalytically active matrix, exposing the plurality of sensing materials and the plurality of constituents in the gas to a temperature above about 400° C., projecting light onto the sensing materials, and detecting the constituents in the gas by a change in the absorption spectrum of the plurality of sensing materials due to the exposure of the plurality of sensing materials to the constituents in the gas at the temperature which causes a chemical reaction in the plurality of sensing materials compared to the absorption spectrum of the plurality of sensing materials in the absence of the constituent in the gas.

In a third aspect, the present invention provides a system for detecting a constituent in a gas containing oxygen. The system includes a sensing material comprising a metal embedded in a catalytically active matrix, a light source for directing light on to said sensing material, a light detector for detecting light reflected from the sensing material, a processor operable to detect the constituent in the gas by a change in the absorption spectrum of the sensing material due to the exposure of the sensing material to the constituent in the gas at the temperature which causes a chemical reaction in the sensing material compared to the absorption spectrum of the sensing material in the absence of the constituent in the gas.

In a fourth aspect, the present invention provides a system for detecting a plurality of constituent in a gas containing oxygen. The system includes a plurality of sensing materials comprising a metal embedded in a catalytically active matrix, a light source for directing light onto said plurality of sensing material, a light detector for detecting light reflected from said plurality of sensing materials, and a processor operable to detect the plurality of constituents in the gas by a change in the absorption spectrum of the a plurality of sensing materials due to the exposure of said plurality of sensing material to the plurality of constituent in the gas at the temperature which causes a chemical reaction in the plurality of sensing materials compared to the absorption spectrum of the plurality of sensing materials in the absence of the constituent in the gas.

BRIEF DESCRIPTION OF THE DRAWINGS

The subject matter which is regarded as the invention is particularly pointed out and distinctly claimed in the concluding portion of the specification. The invention, however, may best be understood by reference to the following detailed description of various embodiments and the accompanying drawings in which:

DETAILED DESCRIPTION OF THE INVENTION

Figure 1:
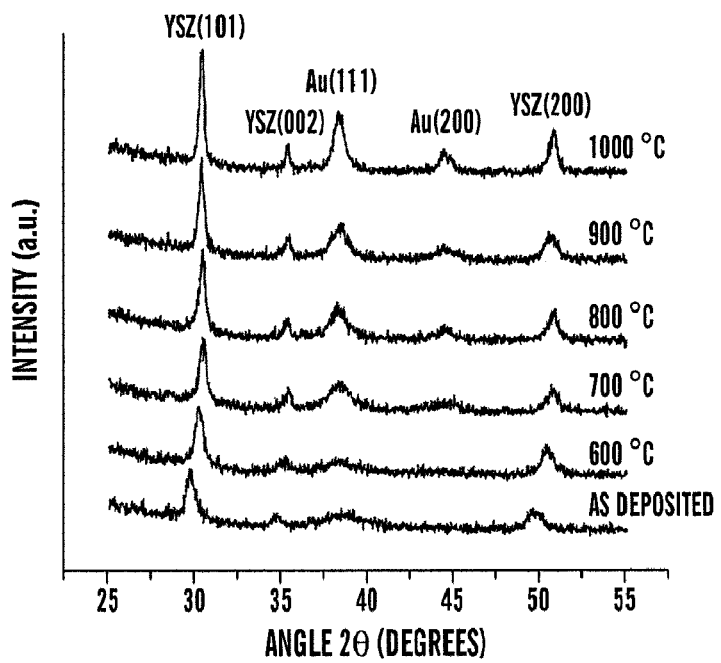
FIG. 1 is an x-ray diffraction (XRD) patterns of Au—YSZ nanocomposite films as a function of annealing temperature.
Figure 2:
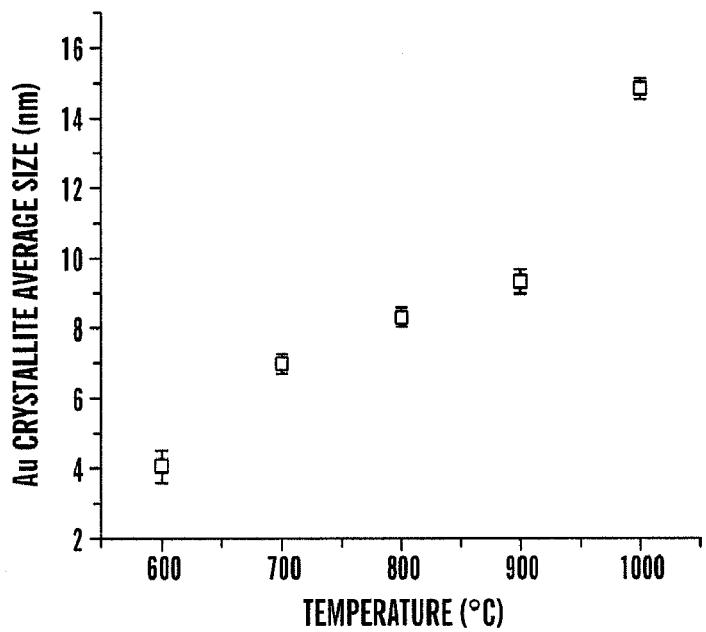
FIG. 2 is a graph of the average Au crystallite size versus annealing temperature wherein the error bars were estimated by an error propagation analysis from the errors in the FWHM and the peak position resulting from a Lorentzian fit to the Au (111) XRD reflection.
Figure 3:
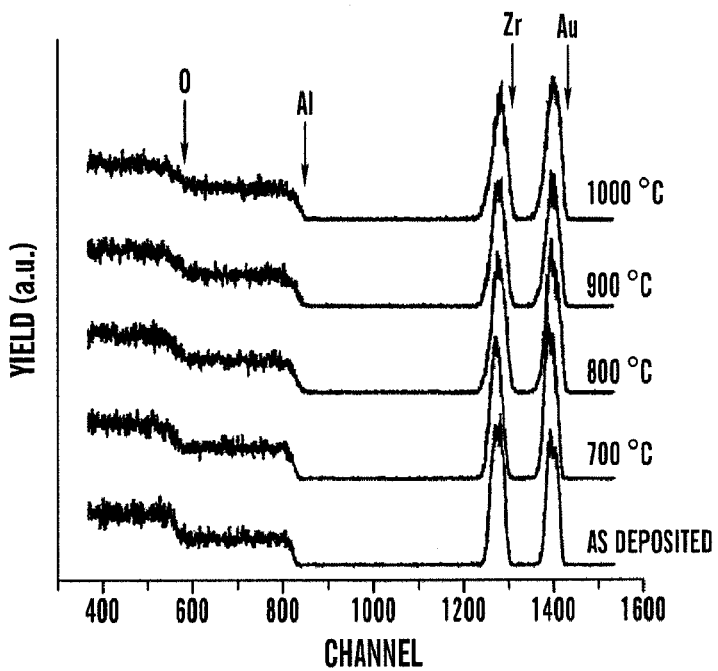
FIG. 3 is an RBS spectra of Au—YSZ nanocomposite films as a function of annealing temperature.
Figure 4:
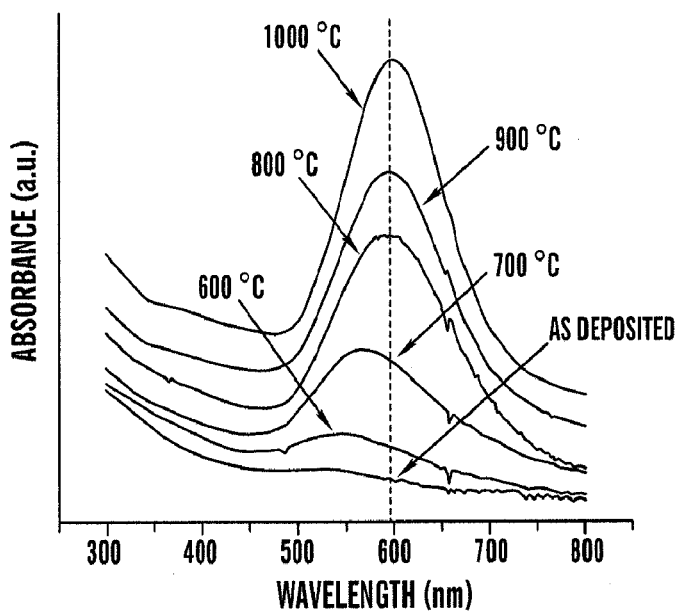
FIG. 4 is an absorption spectra of Au—YSZ nanocomposite films as a function of annealing temperature.

The present invention is directed to sensors for use in high temperature applications above about 400° C. Such applications may include monitoring solid oxide fuel cells (e.g., at temperatures between about 500° C. and about 800° C.), monitoring jet turbine engine emissions (e.g., at about 500° C. to about 800° C.) or other combustion related environments.

In one aspect, the present invention is directed towards extending the operational range of Au nanoparticle based sensing of CO up to about 500° C., to about 600° C., and to about 800° C. through the use of a materials system comprised of Au nanoparticles embedded in an yttria ($Y_2O_3$) stabilized zirconia ($ZrO_2$) matrix. A reversible change in the optical properties of such a gold-yttria stabilized zirconia nanocomposite (Au—YSZ) is observed upon exposure to gas cycles of air and an air/CO mixture. The sensing mechanism has been attributed to interfacial charge transfer chemical reactions occurring at the perimeter of the Au nanoparticles that induce changes in the position and shape of the surface plasmon resonance (SPR) band. These reactions are presumed to be associated with the reduction of the YSZ matrix and the oxidation of CO, via a charge transfer reaction between YSZ bound oxygen anions, formed through the dissociative adsorption of oxygen molecules on YSZ at high temperatures, and the Au nanoparticles, as explained in greater detail below. In another aspect, a target gas for detection with this invention, that reacts on the Au—YSZ material and changes the oxygen anion concentration at this boundary region will induce a change in the absorption spectrum, thus allowing its detection. These other target gases may react via an oxidation mechanism, thereby donating oxygen ions to the nanocomposite, as is the case for the reaction of nitrogen dioxide, or they may react via a reduction mechanism and remove oxygen ions from the nanocomposite, as is the case for carbon monoxide.

In another aspect, the present invention provides a suite of sensing materials for use in a sensing system which provides, for example, active control of gas turbine engines to simultaneously achieve low emissions and high engine efficiencies. This system will be based on the integration of novel nanoparticle based all-optical sensing techniques to meet new regulatory standards proposed by the International Civil Aviation Organization (ICAO), a United Nations intergovernmental body responsible for the worldwide planning, implementation, and coordination of civil aviation. The $NO_x$ ($NO_2$+ NO) emission standards, beginning in 2004, were reduced by 33 percent from standards agreed to in 1981. Furthermore, the ICAO has recommended new certification standards that represent a further 12 percent reduction in NOX, with an effective date of 2008. Aircraft produce a similar suite of emissions as automobiles which include $CO_2$, water vapor, $NO_x$, carbon monoxide, $SO_x$ (sulfur oxides), volatile organic compounds (VOC), particulates, and other trace compounds. However, with aircraft, these emissions primarily take place in the upper tropospheric region and have a significant adverse impact on tropospheric chemistry and are a source for increased greenhouse gases. In particular $NO_x$, CO, and VOC emissions have been shown to negatively affect tropospheric ozone levels. Since the $NO_x$ emission levels from jet turbines are related to the CO and hydrocarbon emissions, all of which can be used as indicators of the engine operating conditions, a sensing system that can monitor all three gases requires an active control system.

Figure 5:
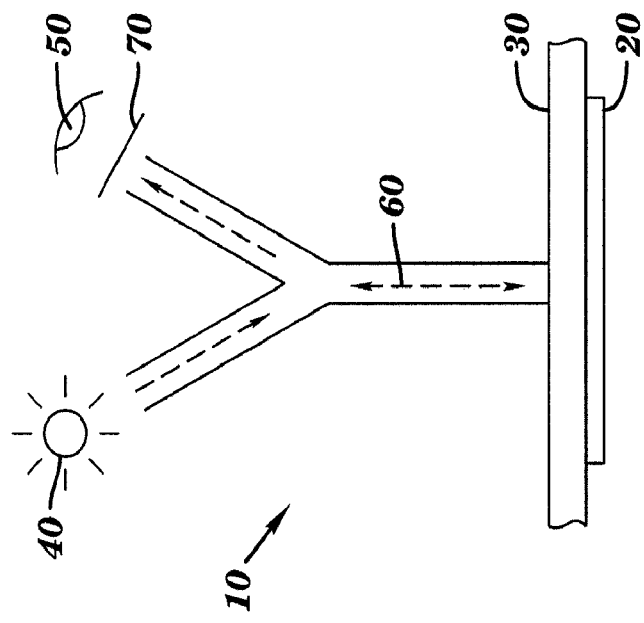
FIG. 5 is one embodiment of a reflective optical gas sensor having a thin film sensing material in accordance with the present invention.

FIG. 5 illustrates one embodiment of a reflective optical sensor 10 having a thin film sensing material 20 in accordance with the present invention deposited on a substrate 30, a light source 40, a light detector 50, and an optical fiber 60. The bifurcated optical fiber 60 directs light from light source 40 to the surface of thin film sensing material 20, and receives and transmits reflected light from the surface of thin film sensing material 20 to detector 50. A filter 70 may be employed to select out the specific frequency of light for analysis as described below. Due to the high temperatures and reactive environments, the substrate may be employed as a window and serve as a sealing surface so that thin film sensing material 20 is exposed to the reactive environment and the other components of the reflective optical sensor are not exposed to the high temperatures and reactive environments. Another example, described in greater detail below, employs use of high temperature compatible fibers (such as sapphire) and the sensing material would be coated directly on the face of the fiber.

Figure 6:
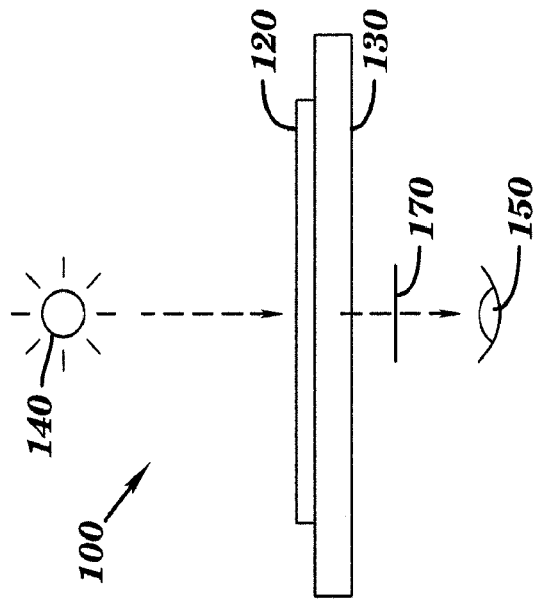
FIG. 6 is one embodiment of a transmission optical gas sensor having a thin film sensing material in accordance with the present invention.

FIG. 6 illustrates one embodiment of a transmission optical sensor 100 having a thin film sensing material 120 in accordance with the present invention deposited on a substrate 130, a light source 140 disposed above thin film sensing material 120, and a light detector 150 disposed below thin film sensing material 120. Light from light source 140 is directed toward a top surface of thin film sensing material 120, transmitted through the thickness of thin film sensing material 120, and the transmitted light from the bottom surface of the thin film sensing material 120 is then detected by detector 150. A filter 170 may be employed to select out the specific frequency of light for analysis as described below. It will be appreciated that the light source could be disposed below thin film sensing material 120 and substrate 130, and the detector can be disposed above thin film sensing material 120 and substrate 130.

The light source and the detector may be operably connected to a microcontroller or processor which is programmed to monitor the detection of a gas as described in greater detail below, and may also be operably connected to one or more output devices for transferring or displaying the results of the detection of the gas. The microcontroller or processor may also be operably connected to one or more storage devices.

With reference again to FIGS. 5 and 6, the thin film sensing materials 20 and 120 may be a Au—YSZ nanocomposite synthesized on sapphire substrates by radio frequency magnetron co-sputtering followed by an ex-situ annealing treatment at about 1,000° C. for between about 2 hours and about 8 hours. By sputtering both the Au and the YSZ at the same time, the resulting thin film includes the gold being dispersed and embedded throughout the YSZ matrix. The annealing treatment stabilizes the film for use at temperatures of about 500° C. and above. The films had a Au content of about 10 at. percent and thickness of about 30 nm. The YSZ films contain about 3 mole percent to 10 mole percent of yttria. An XRD pattern indicated the presence of two polycrystalline phases, one corresponding to the tetragonal phase of YSZ and the other corresponding to the face centered cubic Au phase. The average YSZ and Au crystallite sizes were calculated from the Scherrer formula using the YSZ (101) and the Au (111) reflection, and an average crystallite size of about 19 nm was obtained for both phases for the thin film sensing materials. In many cases, it is desirable for the crystallite size of the Au and the YSZ to be similar in size. These films can be deposited by other means as well to result in the desired composition, grain size (or crystallite size) and film thickness.

Figure 7:
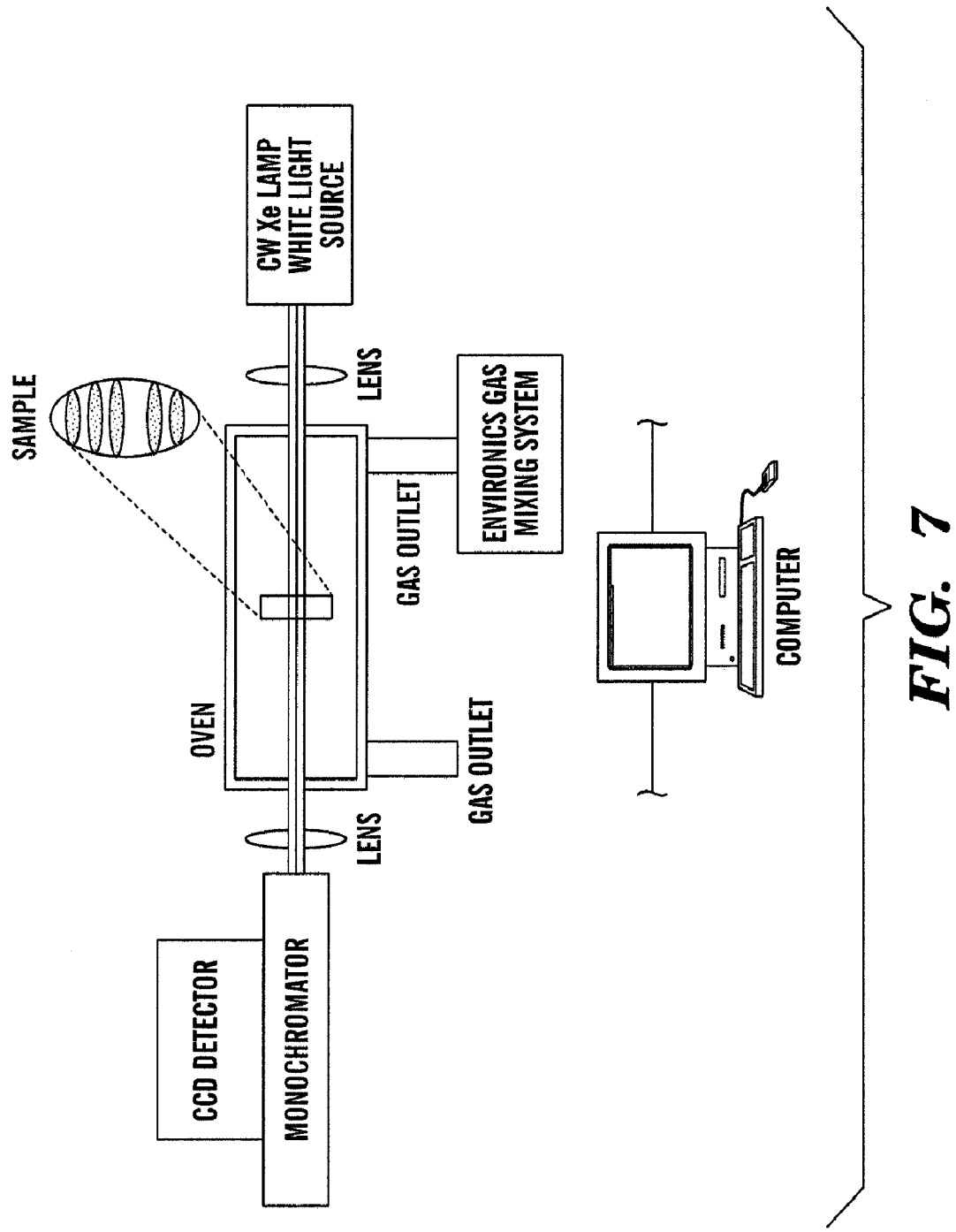
FIG. 7 is a diagrammatic illustration of a test station.

FIG. 7 illustrates a schematic diagram of a testing station. The sensing properties of the films at atmospheric pressure and elevated temperature were tested in a custom-designed quartz transmission cell housed within a tube furnace. White light from a continuous wave xenon (CW Xe) lamp was collimated and transmitted through the sample held centered in the quartz cell using a Macor sample holder. The transmitted light was dispersed and detected using a CCD coupled spectrometer. Air or air/CO (99.998% purity) gas exposures were delivered to the transmission cell via 2 mass flow controllers while maintaining a constant total flow of 2000 sccm.

Oxygen Titration

Figure 8:
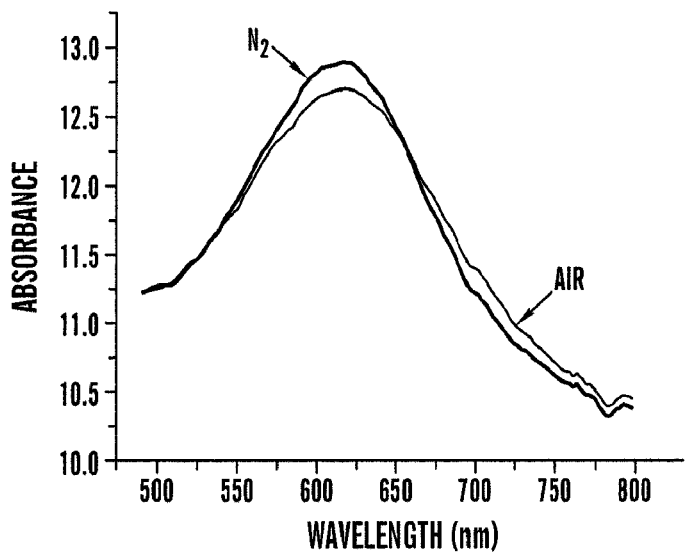
FIG. 8 is a graph of an absorption spectra of Au—YSZ nanocomposite films in air and in a $N_2$ carrier gas at 500° C.

A series of oxygen titration experiments have shown that Au—YSZ nanocomposites for use in sensors have a dependence on the oxygen content present. For example, as shown in FIG. 8, by switching from an $N_2$ gas ($O_2$ free) to an air gas (about 80% $N_2$, about 20% $O_2$) at an operating temperature of 500° C. there was a slight redshift and more notable broadening of the SPR band.

It is understood that the YSZ matrix is an oxygen ion conductor at elevated temperatures, and above a given thermal threshold $O_2$ dissociates on YSZ and generates $O^{2-}$ ions which occupy the vacancies within the crystalline lattice of YSZ.

For example, initially with the temperature between about 500° C. and about 800° C.,

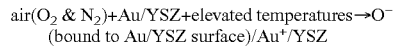

or alternatively,

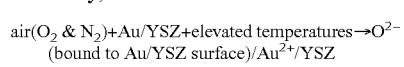

Figure 9:
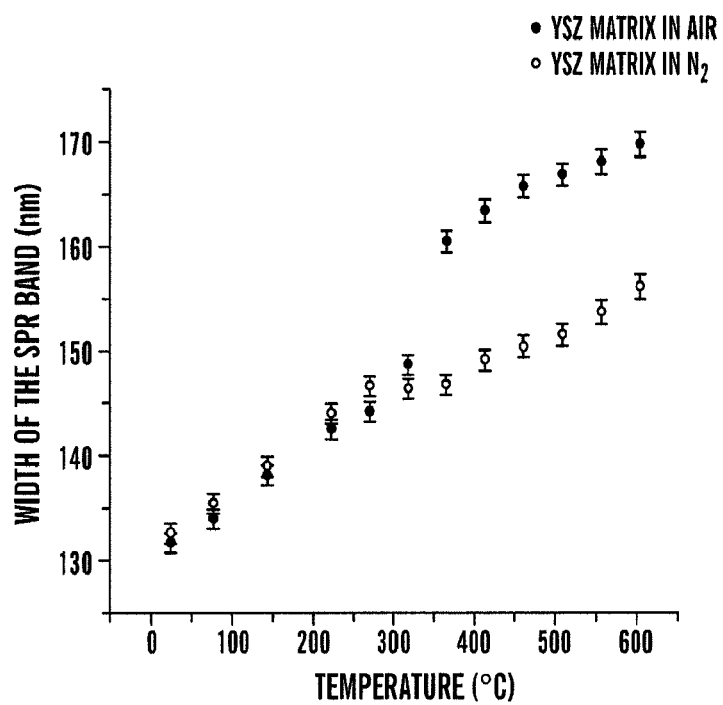
FIG. 9 is a graph of the FWHM of the Au SPR band as a function of operating temperature for both air and $N_2$ carrier gases.

To confirm that the change in the SPR band observed in FIG. 8 was due to the generation of $O^{2-}$ ions, a study of the temperature dependence of the SPR band was conducted in both air and $N_2$ environments. FIG. 9 displays a consistent broadening of the SPR band between room temperature and 600° C. for both carrier gases. This is consistent with the increase in the scattering of the surface plasmons. However, for the air mixture at about 350° C. there is a considerable increase in the FWHM and above this temperature the rate of change in the FWHM is the same as the lower temperature data. This sudden jump in the FWHM occurs at a temperature which is consistent with the onset of $O^{2-}$ formation on the YSZ matrix.

Figure 10:
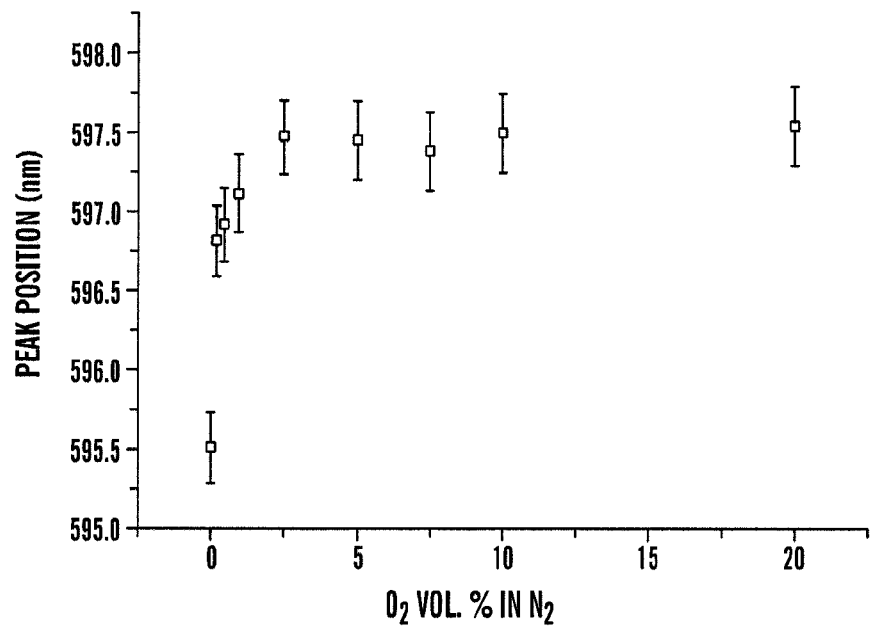
FIG. 10 is a graph of a peak position of the Au SPR band vs. $O_2$ concentration.
Figure 11:
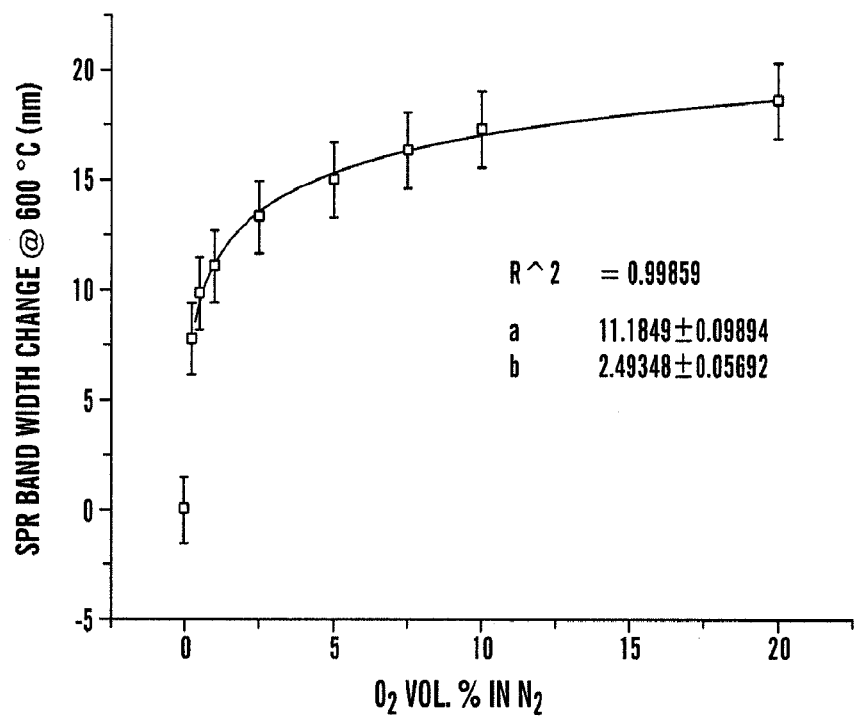
FIG. 11 is a graph of the FWHM of the Au SPR band vs. $O_2$ concentration.

Since the SPR band has an oxygen dependence, a series of oxygen titration experiments which mixed 99.999% pure $N_2$ mixed with 99.999% pure $O_2$ for oxygen concentrations ranging from 0.1% to 10%, with a standard air mixture serving as the data point for 20% $O_2$ in $N_2$. The peak position and the FWHM as a function of the $O_2$ at an operating temperature of 500° C. are shown in FIGS. 10 and 11, respectively. The peak position slightly red shifts at low concentrations and saturates at concentrations above 2.5%, while the FWHM continuously broadens and nearly saturates between the 10 and 20% values. At the prospective operating conditions within a gas turbine (such as combustion environments in jet engines where some of the oxygen is consumed) the oxygen concentrations are typically above 15%, which is above the saturation concentration for both the peak position and the FWHM changes. Since $O^{2-}$ ions will form at this operating temperature, the increase in $O^{2-}$ concentration causes these characteristic changes in the SPR band.

For example, without any $O_2$, there is no measurable sensing signal. For detecting CO, the CO sensing signal is not affected by changes in the O2 concentration above levels which are about 5 vol. % O2. With the detection of $NO_2$ there is a stronger dependence. Therefore, in detecting $NO_2$ there may be a need to monitor the amount of $O_2$ that is present in order to accurately monitor $NO_2$. Other variables that may require monitoring in a complete system may include temperature, oxygen, and humidity.

CO Sensing

Figure 12:
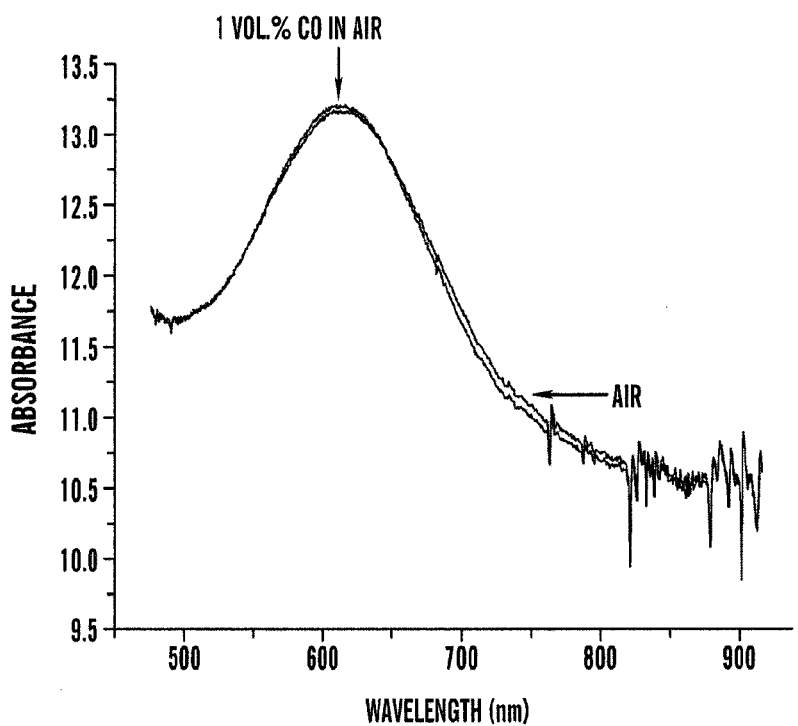
FIG. 12 is a graph of an absorption spectra for air and 1 vol. % CO in air exposures at 500° C.
Figure 13:
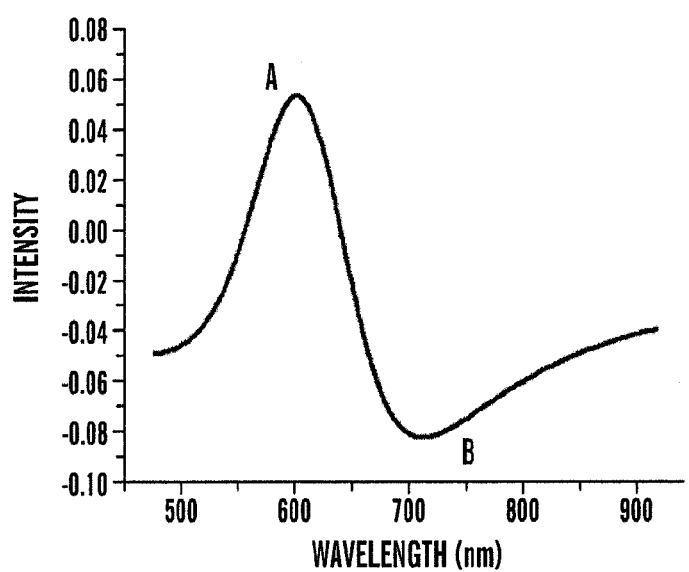
FIG. 13 is a graph displaying the difference spectrum obtained by subtracting the fitted data resulting from the air and the air/CO exposures.
Figure 14:
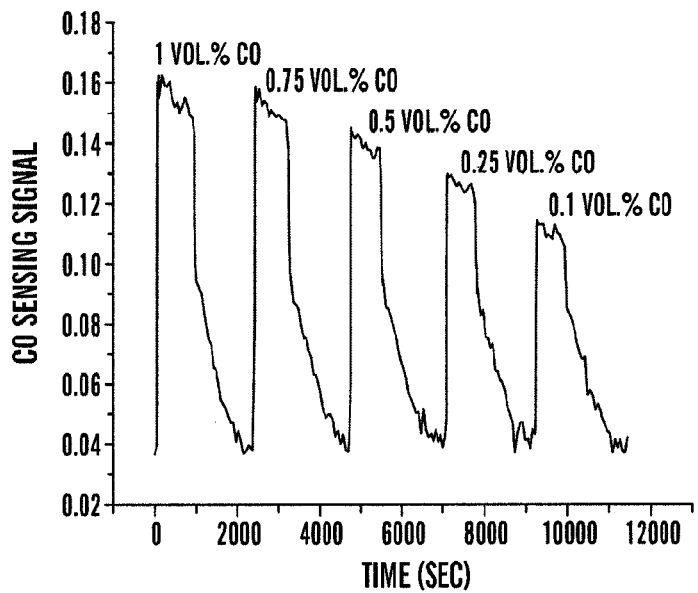
FIG. 14 is a graph of a CO sensing signal vs. time for sequential cycles of CO/air and air gas pulse exposures.

In-situ optical absorption studies of 30 nm thick Au(10 at %)-YSZ films which have been previously annealed to 900° C., resulted in YSZ and Au grain sizes of about 19 nm as determined by X-ray diffraction studies. Sequential exposures to air and CO/air gas pulses at 500° C. resulted in a slight blue shift and a significant narrowing of the SPR band (around 600 nm) as shown in FIG. 12. The data were fitted with Lorentzian curves, and as shown in FIG. 13, the difference spectra was determined from subtracting the gas on and gas off absorption data. The peak-to-peak difference may be readily correlated to the concentration of the CO. The CO sensing signal is taken as the intensity value determined from points A and B in FIG. 13, and a series of CO exposures are shown in FIG. 14. As can be seen, the optical properties reversibly change upon exposure to sequential air and air/CO exposures at an operating temperature of 500° C. The response time of the CO sensing signal is about 40 seconds and the recovery time displays a 2-stage process with a fast, about 60 seconds, and slow, about 1000 seconds, recovery time. The sensing mechanism has been attributed to high temperature interfacial charge transfer chemical reactions, occurring at the perimeter of the Au nanoparticles, which inject charge into the Au nanoparticle, causing changes in both the position and shape of the SPR band. These reactions are presumed to be associated with the reduction of the YSZ matrix and the oxidation of CO, via a charge transfer reaction between YSZ bound oxygen anions, formed through the dissociative adsorption of oxygen molecules on YSZ at high temperatures, and the Au nanoparticles.

For example, upon reaction of the surface bound $O^-$ ion (or $O^{2-}$) and the CO molecule, the electron previously bound to the $O^-$ ion (or $O^{2-}$) is donated back to $Au^+$ (or $Au^{2+}$) thus neutralizing (or reducing the positive charge) on the Au nanoparticle and causing the "blue shift" and narrowing of the surface plasmon resonance band of the Au nanoparticle as follows, $$O^-/Au^+/YSZ+CO+air(O_2 \& N_2) \rightarrow CO_2+Au/YSZ+air(O_2 \& N_2)$$

or alternatively, $$O^{2-}/Au^{2+}/YSZ+CO+air(O_2 \& N_2) \rightarrow CO_2+O^-/Au^+/YSZ+air(O_2 \& N_2).$$

CO exposure studies in the absence of oxygen at 500° C. observed no change in the SPR band, while CO exposures as a function of temperature likewise did not produce a change in the SPR band until temperatures exceeded about 350° C., which is the same temperature required for $O^{2-}$ formation and transport within YSZ materials.

Figure 15:
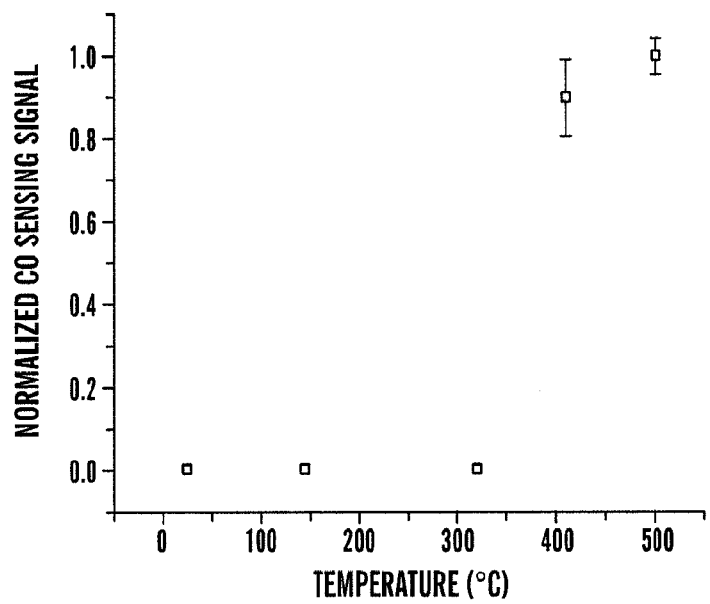
FIG. 15 is a graph of a CO sensing signal for 1% exposures as a function of the reaction temperature.

Temperature dependence of the CO reaction and its corresponding change in the Au nanoparticle SPR band were also studied. Exposure studies from room temperature to 500° C. have been performed for 1% CO mixtures in air as shown in FIG. 15. As can be seen the 1% CO exposures have no affect on the SPR band for temperatures below 325° C. and then suddenly turn on at 400° C. and 500° C. Again this onset in the reaction is consistent with the $O^{2-}$ formation temperature on the YSZ matrix.

Hydrogen Sensing

As the formation of $O^{2-}$ is a prerequisite for the oxidation of CO it is likely that the reaction of $H_2$ with $O^{2-}$, or the catalytic reaction of hydrocarbons would also be observable and may cause selectivity problems for these sensing materials. For example, upon reaction of the surface bound $O^-$ ion (or $O^{2-}$) and the $H_2$ molecule, the electron previously bound to the $O^-$ ion (or $O^{2-}$) is donated back to $Au^+$ (or $Au^{2+}$) thus neutralizing (or reducing the positive charge) on the Au nanoparticle and causing the "blue shift" and narrowing of the surface plasmon resonance band of the Au nanoparticle as follows, $$O^-/Au^+/YSZ+H_2+air(O_2 \& N_2) \rightarrow H_2O+AU/YSZ+air(O_2 \& N_2)$$

or alternatively, $$O^{2-}/Au^{2+}/YSZ+H_2+air(O_2 \& N_2) \rightarrow H_2O+O^-/Au^+/YSZ+air(O_2 \& N_2).$$

Figure 16:
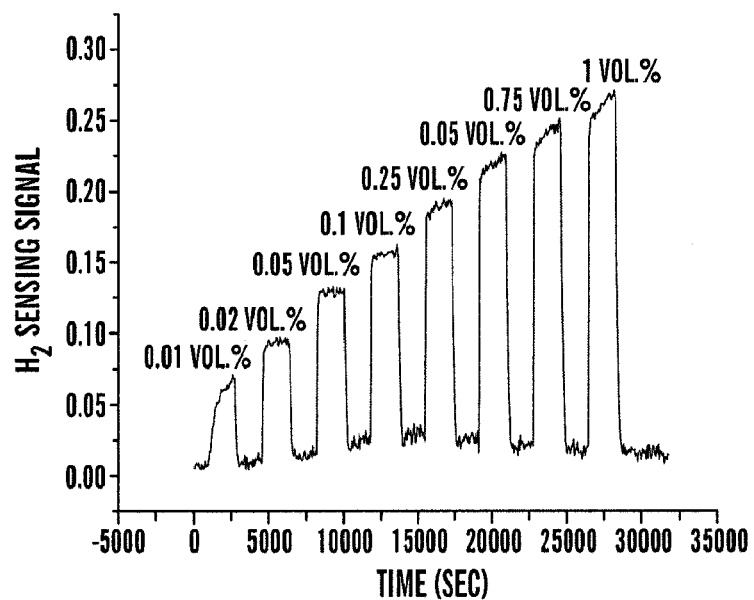
FIG. 16 is a graph of a $H_2$ sensing signal as a function of time for repeated 0.01, 0.02, 0.05, 0.1, 0.25, 0.5, 0.75 and 1% $H_2$ in air exposures at 500° C.
Figure 17:
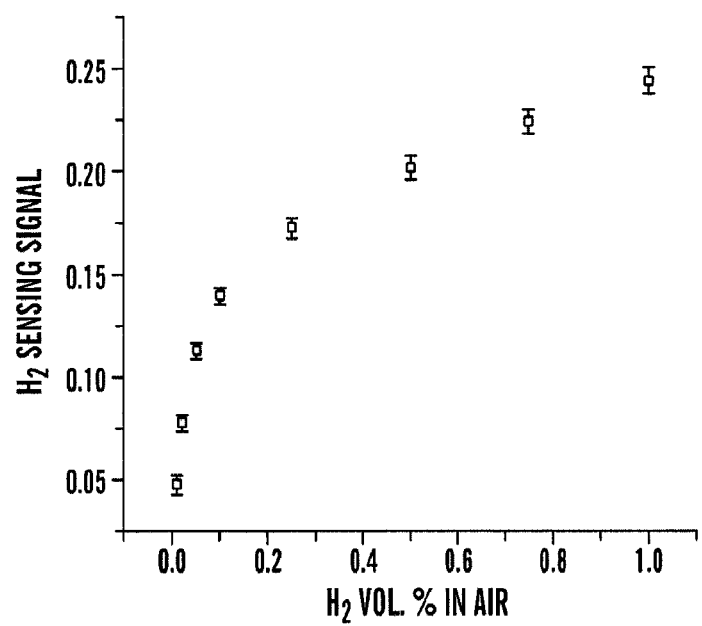
FIG. 17 is a graph of the $H_2$ sensing signal vs. $H_2$ concentration.

Using hydrogen ($H_2$) as a test gas with the Au—YSZ films, hydrogen exposures cause a blue shift and a narrowing of the SPR band. The data analysis of these reactions was performed in a similar manner as done for the CO studies. The $H_2$ sensing signal is shown in FIG. 16 and has a comparable response time of about 40 seconds, while the recovery time has only one stage and is comparable to the response time. A difference for the films used in the hydrogen studies is that the Au nanoparticle size was about 25 nm after a 9 hour annealing preparation in argon at 1000° C. The $H_2$ sensing signal vs. $H_2$ concentration is plotted in FIG. 17 and shows a non-linear behavior between 0.01% and 1% $H_2$ concentrations.

Figure 18:
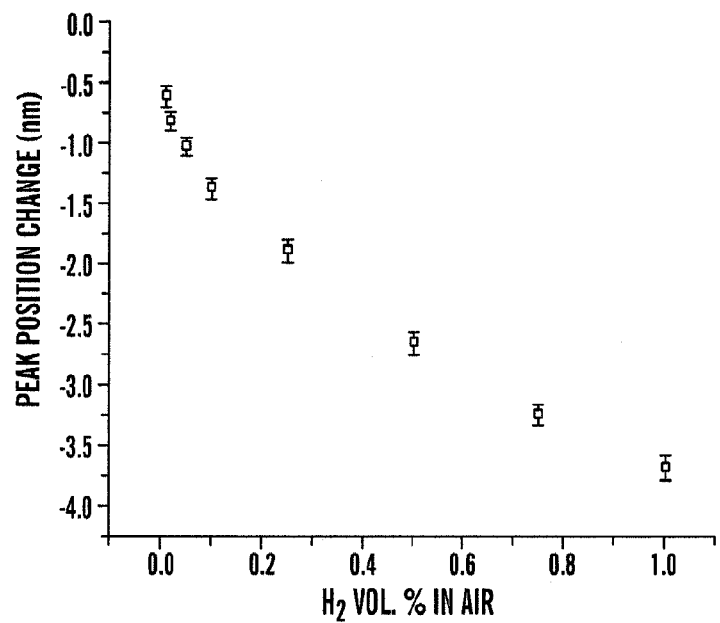
FIG. 18 is a graph of an Au SPR band peak position vs. $H_2$ concentration.
Figure 19:
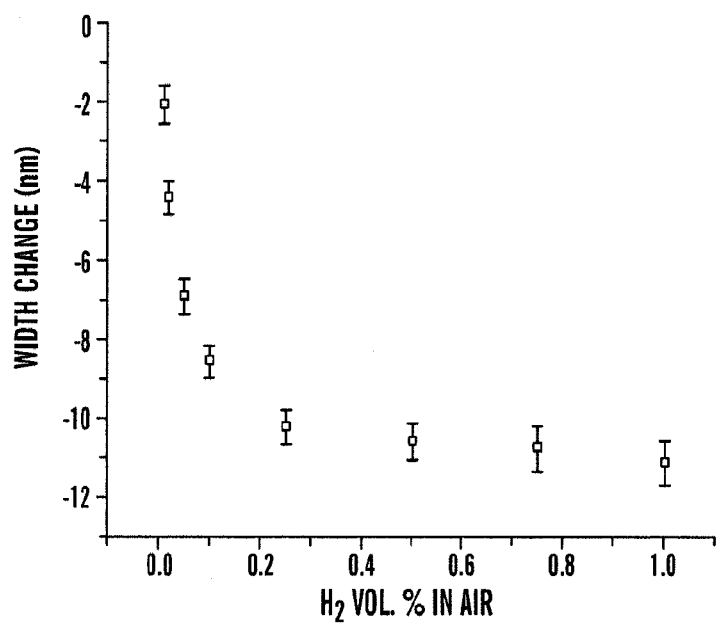
FIG. 19 is a graph of an Au SPR band FWHM vs. $H_2$ concentration.

Since the sensing signal contains contributions from both the change in the SPR peak position and the FWHM, plots of the peak position and the FWHM vs. $H_2$ concentration are show in FIGS. 18 and 19 which display the SPR band peak position and the FWHM vs. $H_2$ concentration respectively. While the peak position dependence on $H_2$ concentration is non-linear in nature it has a continuous blue shift characteristic with increasing $H_2$ concentrations. However, the FWHM dependence in FIG. 18 strongly narrows at low $H_2$ concentrations and then nearly plateaus at concentrations higher than 0.2%. The change in $O^{2-}$ ion concentrations is due to the reaction of $H_2$ with the Au—YSZ matrix affects the optical properties of the Au nanoparticles in a characteristic fashion.

$H_2$ Selectivity

Figure 20:
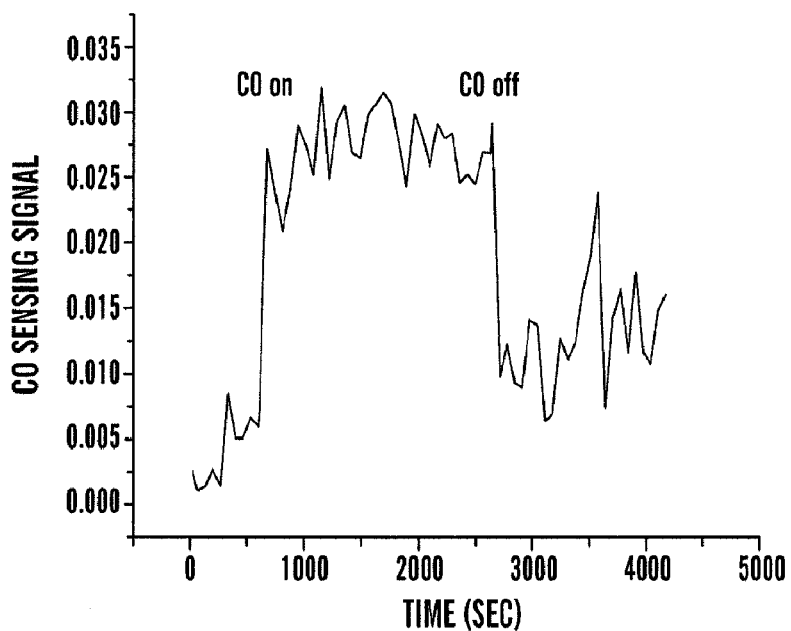
FIG. 20 is a graph of a CO sensing signal for a 1% CO exposure vs. time.
Figure 21:
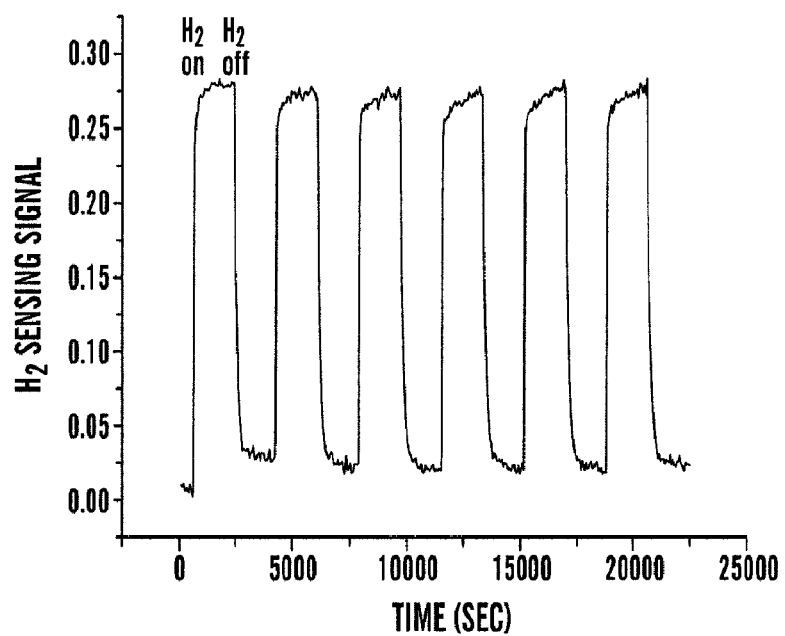
FIG. 21 is a graph of an $H_2$ sensing signal for a 1% $H_2$ exposure vs. time.

The sensing films developed for the hydrogen sensing tests were also exposed to 1% CO cycles for a comparison of the sensing capabilities. FIG. 20 displays the CO sensing signal for a 1% CO in air mixture at an operating temperature of 500° C., and as can be seen, the CO sensing signal is a factor of 6 less than as observed with films having a 19 nm particle size. More so, as shown in FIG. 21 the 1% CO sensing signal is only 8% of the value obtained for the 1% $H_2$ in air sensing signal. Therefore, these tests show that the use of sensing films having smaller Au particles works better for the detection of CO. It is believed that the detection of constituents may be dependent on both the particle diameter and on the atomic or cluster Au content. From our previous study we determined that the films prepared with annealing temperatures below 800° C. had a significant amount of atomic gold as determined by spectroscopic ellipsometry. The higher CO catalytic activity of these cluster gold containing films is consistent with the studies performed on the catalytic oxidation of CO on Au—$ZrO_2$ and Au—$TiO_2$ materials.

$H_2$ Temperature Dependence

Figure 22:
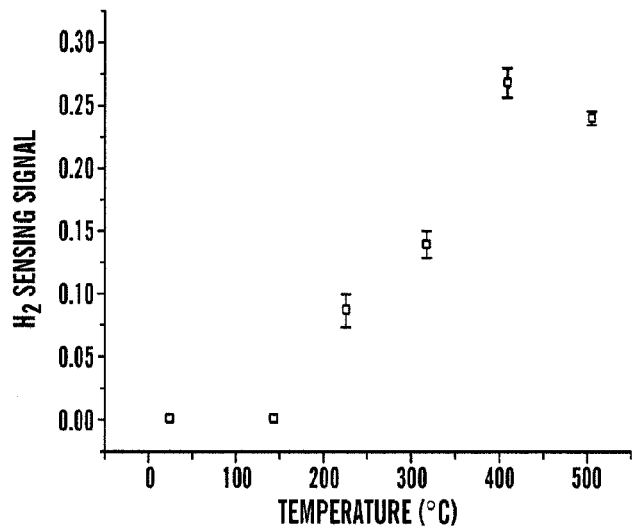
FIG. 22 is a graph of the sensing signal dependence on temperature for 1% $H_2$ in air exposures.

The temperature dependence of the $H_2$ reaction is shown in FIG. 22 for 1% hydrogen in air exposures with no change observed in the SPR band at room temperature. The reaction onset appears at a lower temperature than observed for the CO reactions at about 200° C., which is still consistent with the onset of the $O^{2-}$ formation on YSZ matrices. The $H_2$ sensing signal change appears to saturate at 400° C. and 500° C.

$H_2$ Titration Experiments with Oxygen-500° C.

Figure 23:
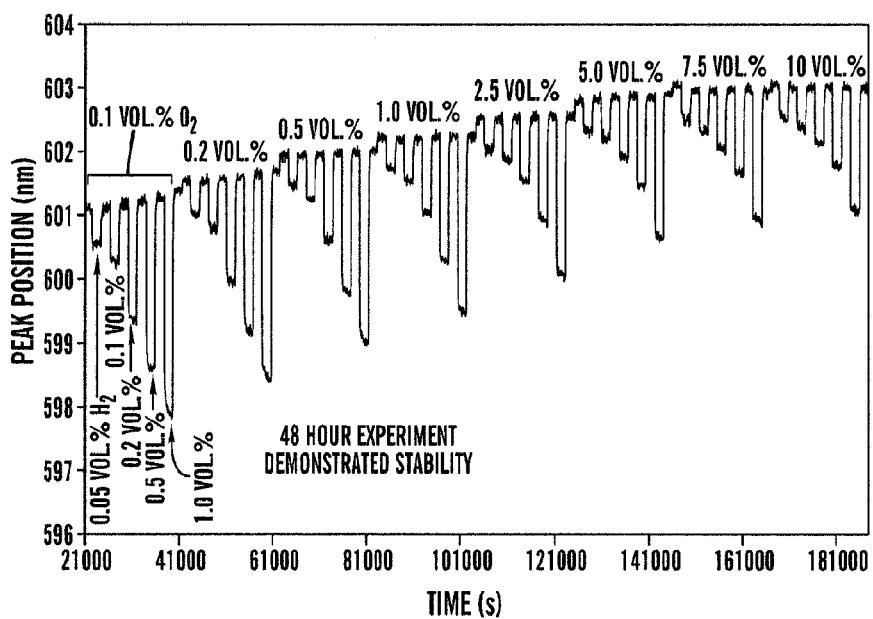
FIG. 23 is a graph of the peak position vs. Time for 0.05, 0.1, 0.2, 0.5, and 1 vol. % hydrogen exposures with 0.1, 0.2, 0.5, 1.0, 2.5, 5, 7.5 and 10 vol. % oxygen levels.
Figure 24:
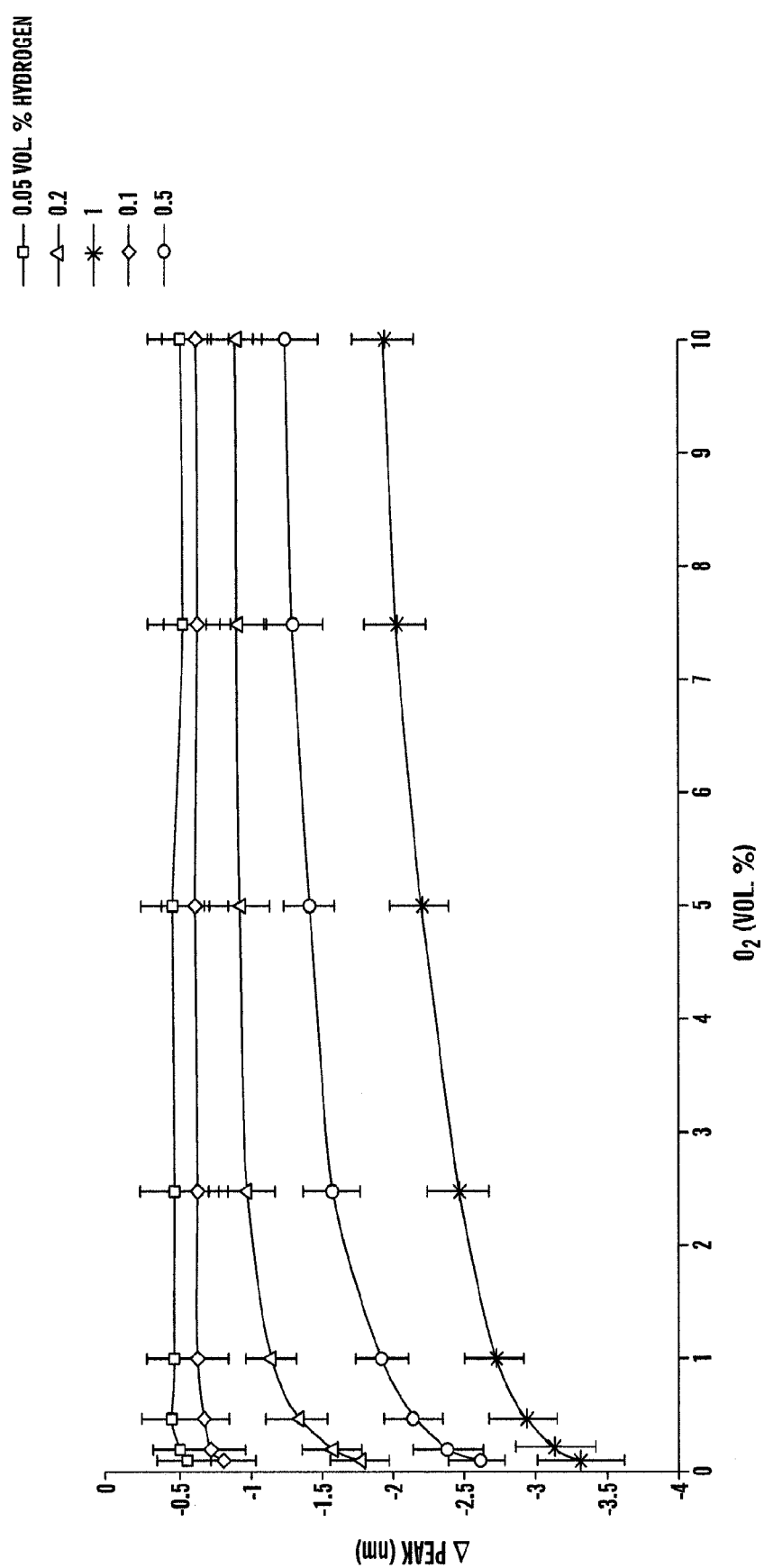
FIG. 24 is a graph of the peak position change vs. $O_2$ concentration for 0.05, 0.1, 0.2, 0.5 and 1.0 vol. % hydrogen concentrations.
Figure 25:
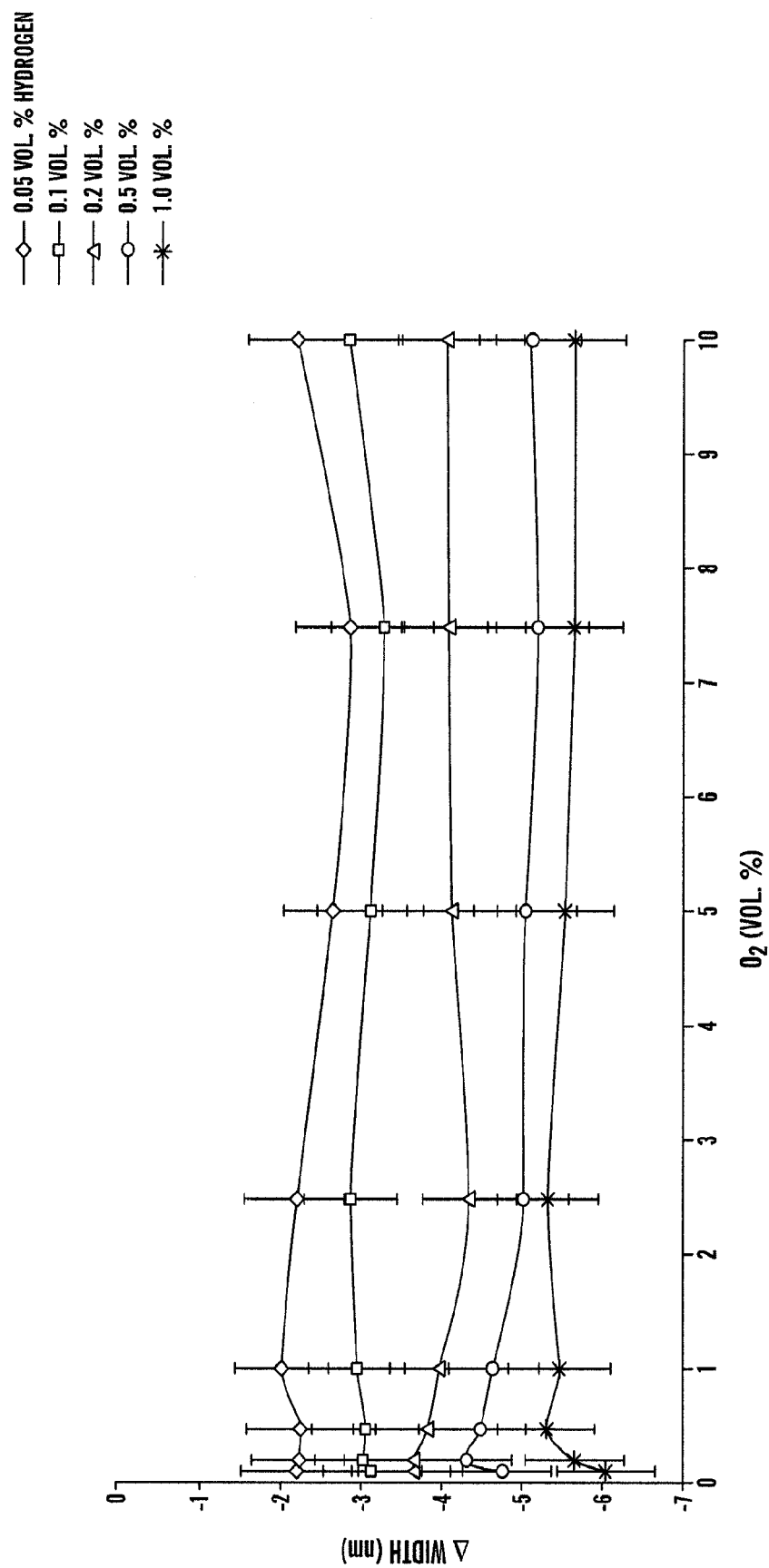
FIG. 25 is a graph of the FWHM change vs. $O_2$ concentration for 0.05, 0.1, 0.2, 0.5 and 1.0 vol. % hydrogen concentrations.

Titration experiments with varying amounts of oxygen have been performed with oxygen concentrations equaling 0.1, 0.2, 0.5, 1.0, 2.5, 5.0, 7.5 and 10 volume % with hydrogen concentrations of 0.05, 0.1, 0.2, 0.5 and 1.0 volume % at each of the individual oxygen concentrations. These experiments were performed in one continuous run and the results are shown in FIGS. 23-25. FIG. 23 illustrates the change in the SPR band peak position as a function of time from t=2,100 s till t=18,100 s, which is just about a 5 hour snapshot of the full 48 hour experiment that repeated the set of gas cycles in FIG. 23 several more times. As can be seen in the figure the baseline peak position of the SPR band, while being exposed to increasing oxygen concentrations, shifts continuously from about 601 nm to about 603 nm. This shift to longer wavelengths is indicative of more $O^{2-}$ being formed within the matrix which causes the positive charge to increase on the gold nanoparticles leading to the red shift in the SPR band.

These results are consistent with those observed in the initial oxygen titration experiments displayed in FIGS. 10 and 11.

During the hydrogen exposure cycles the hydrogen reacts with the $O^{2-}$ forming water and donating the electrons back to the gold nanoparticle causing the reversible blue shift in the SPR band. As can be seen from this figure the change in the peak of the SPR band is reversible and it is apparent that at low oxygen concentrations there is more contrast in the peak position change than at higher oxygen concentrations, which is more apparent in FIG. 24 which plots the change in peak position vs. $H_2$ concentration and $O_2$ concentration. The increase in contrast at lower $O_2$ concentrations is likely due to the fact that both the hydrogen reaction with the $O^{2-}$ to form water and the background $O_2$ reaction with the YSZ matrix to form more $O^{2-}$ are competitive reactions whose shift in equilibrium is affected by the change in the reagent concentrations. This results in a greater blue shift for hydrogen exposures at lower oxygen concentrations, while at higher oxygen concentrations the equilibrium shifts towards the formation of more $O^{2-}$ thus resulting in a smaller blue shift upon exposure to hydrogen. The hydrogen reaction has a strong dependence on oxygen concentrations below 5%, while above these concentrations there is no change in peak position, and thus for operating conditions with $O_2$ levels between 5 and 20% (air) the hydrogen detection characteristics are independent of oxygen which is similar to that observed for carbon monoxide. FIG. 25 plots the change in the FWHM of the SPR band as a function of both hydrogen and oxygen concentrations, and as seen in this figure, the change in FWHM has no strong dependence on oxygen concentration.

$NO_2$ Sensing

A series of exposure studies demonstrate the reversible detection of $NO_2$ showing a detection limit of 5 ppm at 500° C. in the presence of air. The reaction of $NO_2$ on the Au—YSZ matrix is significantly different than the $H_2$ and CO studies. While $H_2$ and CO react with the $O^{2-}$, $NO_2$ reacts on the hot gold particles forming NO and O atoms. The O atoms then subsequently react at the tri-phase boundary forming $O^{2-}$ ions and remove electrons from the Au nanoparticles causing a red shift in the SPR band similar to that observed for $O_2$ reacting with the AU-YSZ matrix.

For example, upon reaction at the $O^-/Au^+/YSZ$ interface, $NO_2$ is converted to NO and an O atom. The O atom is converted to $O^-$ by removing an electron from the Au nanoparticle, thus causing a further redshift and broadening of the surface plasmon resonance band of the Au nanoparticle,

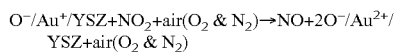

or alternatively,

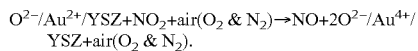

Figure 26:
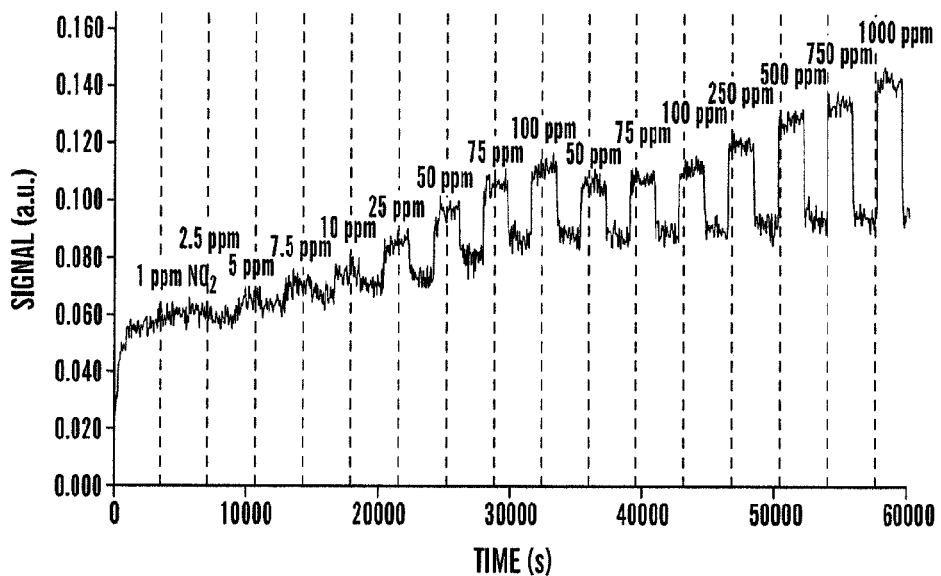
FIG. 26 is a graph of the sensing signal vs. time for a series of NO2 exposures in air at 500° C.
Figure 27:
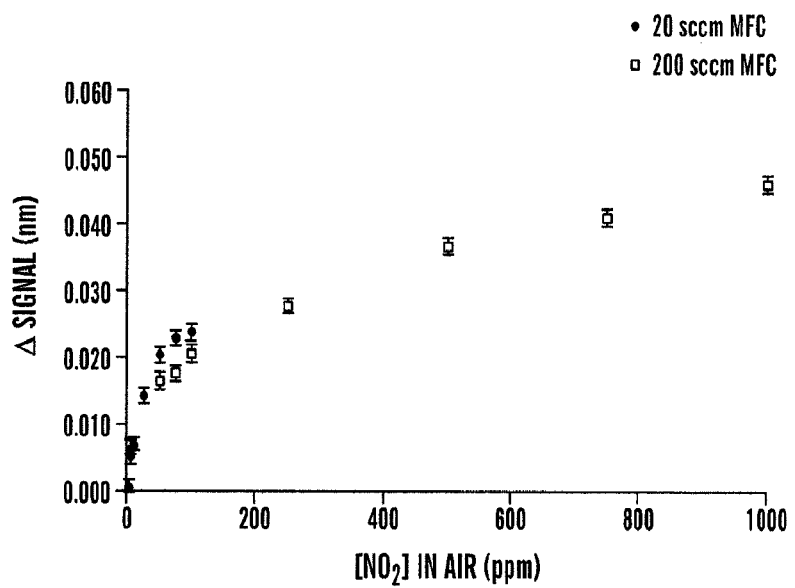
FIG. 27 is a graph of the signal change vs. $NO_2$ concentration for 500° C. in air.

A series of $NO_2$ exposure experiments were performed at an operating temperature of 500° C. with $NO_2$ concentrations from 1 ppm to 100 ppm as shown in FIG. 26 which displays sensing signal vs. time. The $NO_2$ detection limit as seen in this figure is 5 ppm with reversible signal changes observed over the entire 3 day experiment. To obtain such a wide range of exposure concentrations we used a 20 and a 200 sccm mass flow controller with 3 concentrations, as shown in FIG. 27, of overlapping concentrations to ensure data continuity between runs. FIG. 27 displays the signal change plotted vs. $NO_2$ concentration which indicates a logarithmic type response over the range of concentrations that were studied. As indicated in the above reaction scheme, $NO_2$ would not require any oxygen to be present in order to induce a signal change in the SPR band. In fact the extra oxygen present in the Au—YSZ matrix would likely cause the detection limit for $NO_2$ to be lower as the matrix is nearly saturated with $O^{2-}$ ions as indicated in the original oxygen titration data displayed in FIGS. 10 and 11.

Figure 28:
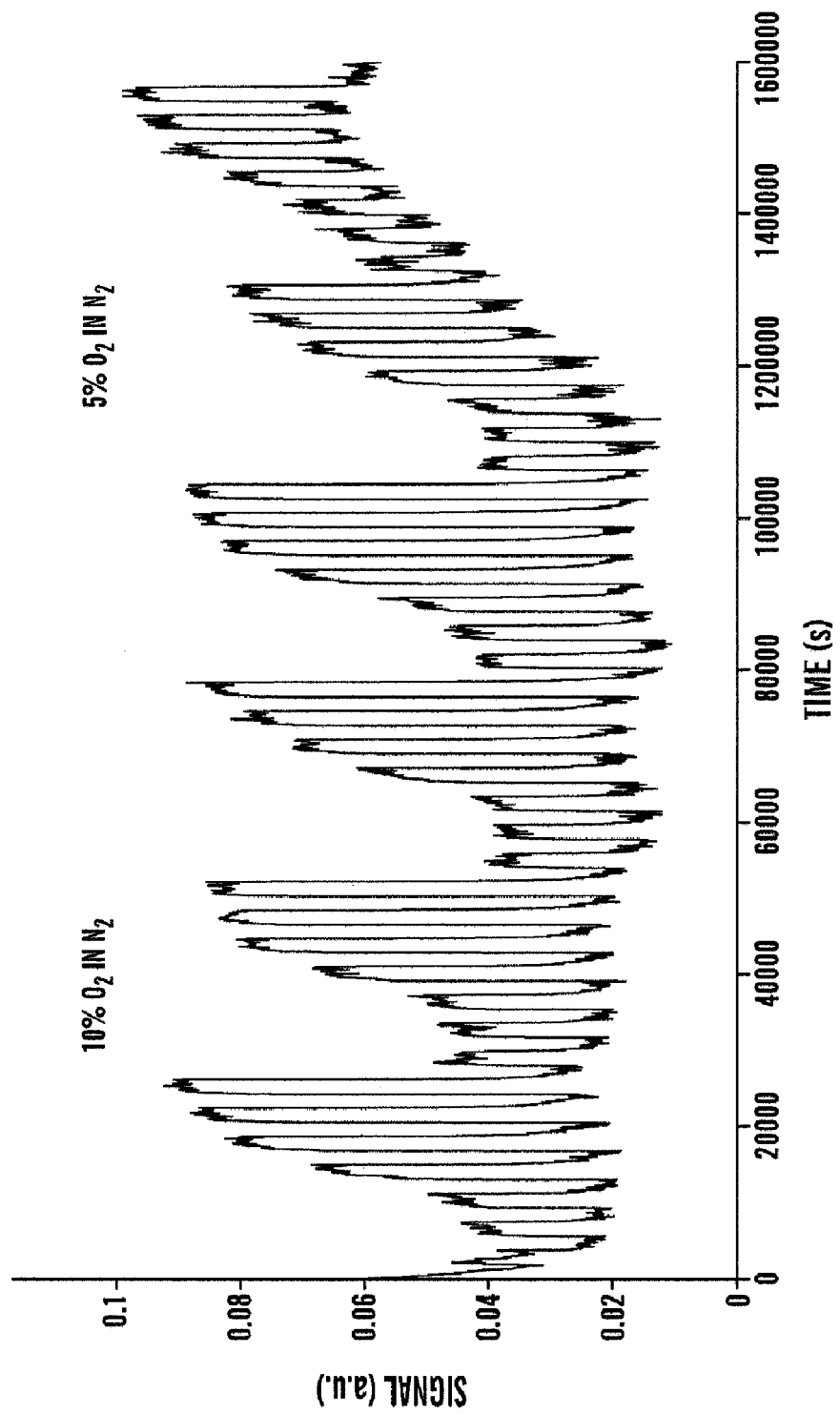
FIG. 28 is a graph of the sensing signal vs. time for $NO_2$ exposures with 5 and 10 vol. % oxygen at an operating temperature of 500° C.
Figure 29:
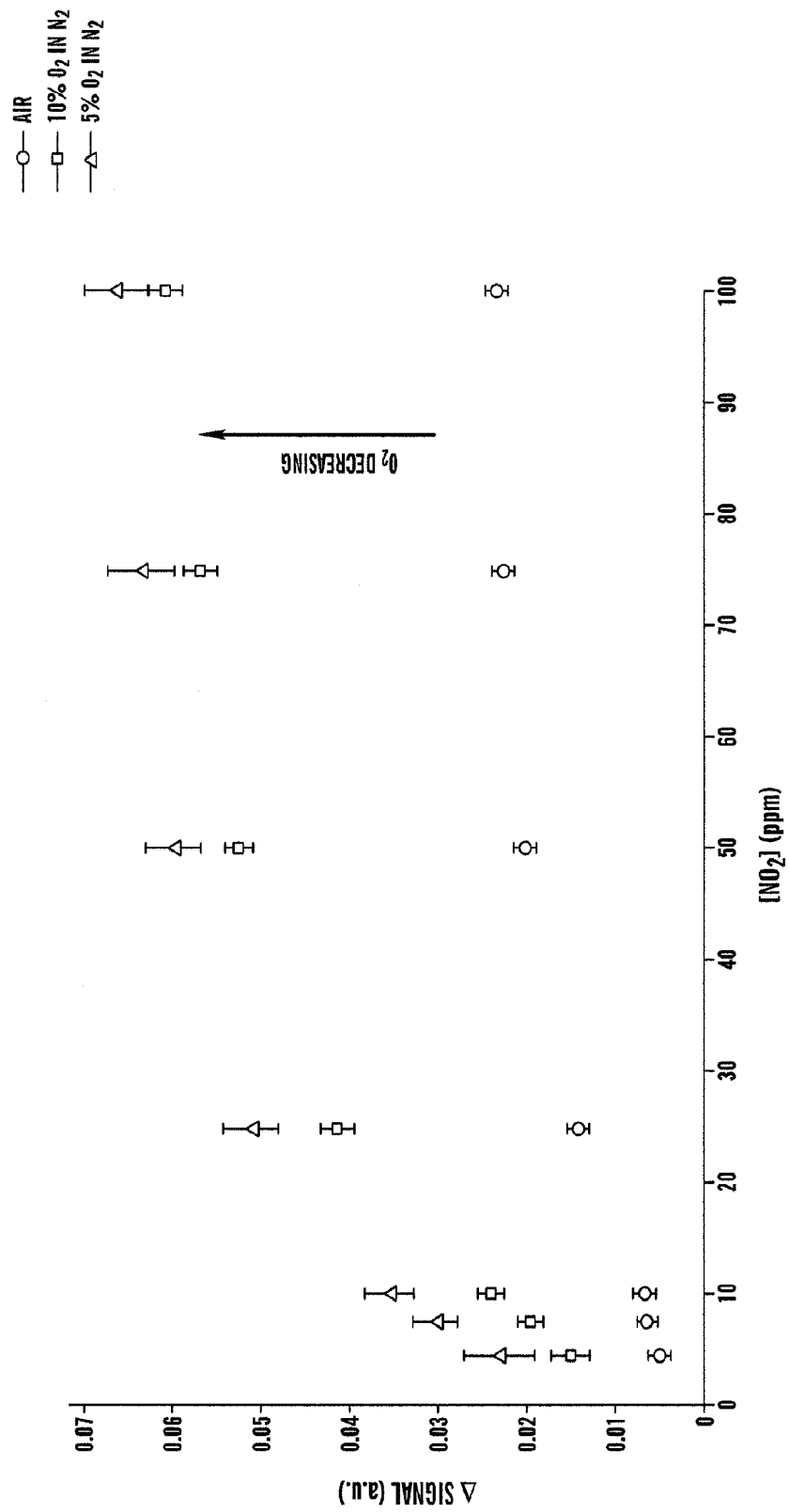
FIG. 29 is a graph of the signal change vs. $NO_2$ concentration for air and 10 and 5 vol. % $O_2$ concentrations in nitrogen.

To probe the details of the oxygen dependence, experiments at 5 and 10 vol. % oxygen in a nitrogen carrier gas with $NO_2$ concentrations were performed that included 5, 7.5, 10, 25, 50, 75 and 100 ppm. As seen in FIG. 28, which plots the sensing signal vs. time for a 10 and 5 vol. % oxygen levels, it is apparent that $NO_2$ is still reversibly detected and the observed signal change at all $NO_2$ concentrations is higher than for $NO_2$ in air. In order to directly compare the signal changes for the 3 oxygen concentrations, a plot of the signal change vs. $NO_2$ concentrations for 5, 10 and 20 vol. % oxygen levels is shown in FIG. 29. As expected since the $NO_2$ reaction does not require oxygen to cause a signal change, when the oxygen levels are reduced, thus causing the matrix to have a smaller background concentration of $O^{2-}$, and allowing the $NO_2$ reaction to induce a greater signal change at each of the $NO_2$ exposure concentrations. In fact, as seen in this figure, the signal change at 5 ppm $NO_2$ concentrations is a factor of about 5 higher which means that at reduced oxygen concentrations the detection limit for $NO_2$ likely approaches a 1 ppm limit. However, implementation of the Au—YSZ nanocomposite for the detection of $NO_2$ in environments with oxygen levels ranging from 5 to 20 vol. % may require the complementary detection of oxygen as the $NO_2$ reactions are oxygen dependent with regards to the $O^{2-}$ degree of saturation within the Au—YSZ matrix.

Figure 30:
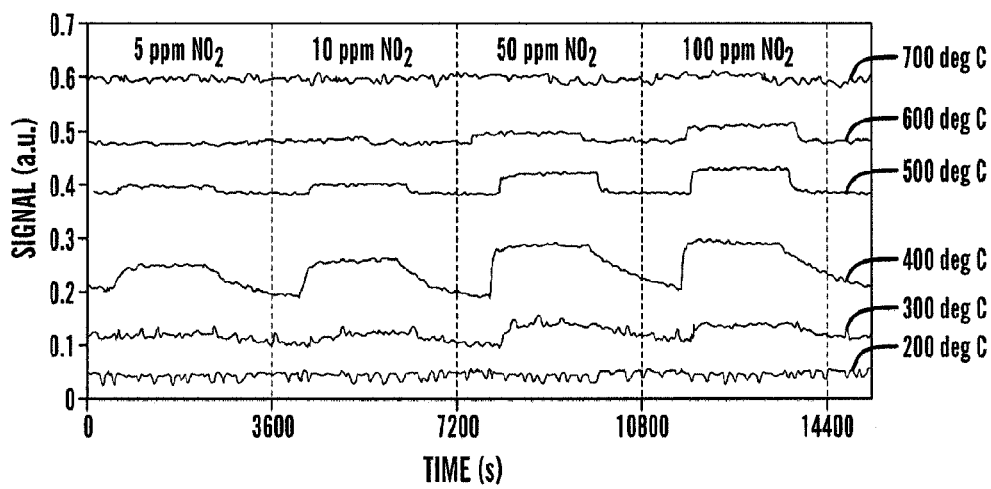
FIG. 30 is a graph of the sensing signal vs. time for 5, 10, 50 and 100 ppm $NO_2$ exposures in air at 200, 300, 400, 500, 600 and 700° C. operating temperatures.

The temperature dependence of the $NO_2$ reactions was also studied to determine whether these reactions have a similar dependence as the $H_2$ and CO reactions. Even though $NO_2$ does not require $O^{2-}$ ions for its reaction, the O atoms formed upon the initial reaction of $NO_2$ on the hot gold surface do require the ability to subsequently form $O^{2-}$ ions to remove electrons from the gold nanoparticle to induce a measurable change in the SPR band. Therefore, a similar temperature dependence is expected as observed for $H_2$ and CO. FIG. 30 shows the signal change vs. time for $NO_2$ concentrations of 5, 10, 50 and 100 ppm for reaction temperatures of 200, 300, 400, 500, 600 and 700° C. As expected at an operating temperature of 200° C., signal change upon $NO_2$ exposure was not observed, while at 300° C. the $NO_2$ started to become detectable. An operating temperature of 400° C. had the largest signal change while above this temperature the signal change decreased and at 700° C., $NO_2$ is not detectable at these concentrations. While the signal change at 400° C. is the largest its corresponding time response and recovery characteristics are both much slower than at 500 or 600° C. and in fact at 400° C. the signal change never saturates within the 30 minute gas exposure window and it never recovers within the 30 minute recovery window. These poor time characteristics are interesting and may be an indication of the near saturation of the Au—YSZ matrix with $O^{2-}$ ions due to the background reactions of $O_2$ at 20 vol. % concentrations causing the number of active sites available for reaction to be significantly reduced, leading to longer response and recovery times at lower operating temperatures. Such poor time characteristics were not observed for the $H_2$ or CO studies as these reactions removed $O^{2-}$ from the matrix rather than a donation of $O^{2-}$ as required for the $NO_2$ reactions. The reactions at operating temperatures of 500 and 600° C. have an added amount of available energy which increases the diffusion times of the active species thus leading to faster response and recovery times. Analysis of the response times at 500° C., which is defined as the time required for the signal to go from its baseline value before NO$_2$ exposure to a fully saturated signal change during NO$_2$ exposure is 240 seconds and 215 seconds for the 5 and 100 ppm exposures respectively in FIG. 30. The reduced signal changes observed for the 500 and 600° C. operating temperatures compared with the signal change observed at 400° C. is likely due to the competition of both NO$_2$ and O$_2$ reacting with the Au—YSZ nanocomposite and each attempting to form O$^{2-}$ ions on a finite number of reaction sites. With O$_2$ in significant excess with respect to NO$_2$, it is apparent that the O$_2$ reactions are more efficient at the higher operating temperatures which leads to a loss of detection of NO$_2$ at the higher operating temperatures. The details of the reaction dynamics of NO$_2$ as a function of operating temperature may require more detailed studies as a function of both temperature and oxygen concentrations with studies that would have oxygen completely removed to deconvolute the NO$_2$ dependence on operating temperature.

Figure 31:
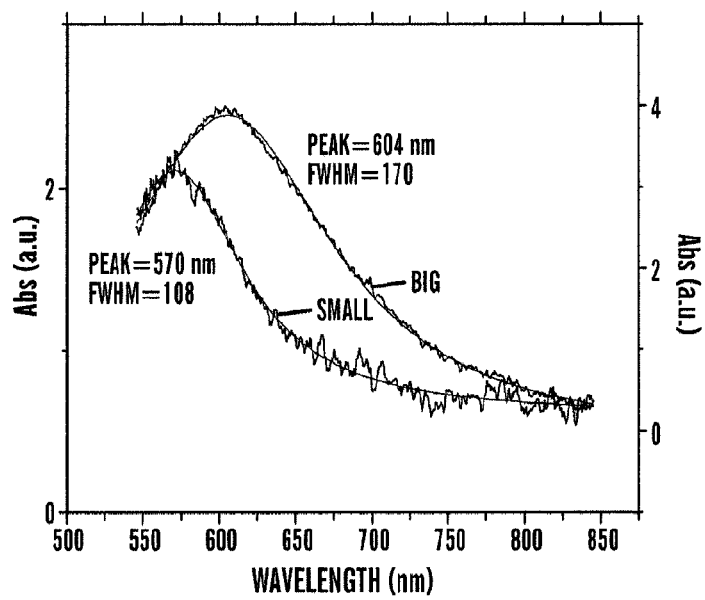
FIG. 31 is an overlay of SPR bands for two Au—YSZ films annealed to produce Au nanoparticles with about 10 and about 23 nm diameters.

As with hydrogen and CO testing we have also performed initial studies on the size dependence of the NO$_2$ sensing reaction as a function of particle size. A Au—YSZ film containing 10 at. % Au and with a thickness of about 30 nm was deposited onto a sapphire sample and annealed at 900° C. for 2 hours in an argon carrier gas. The resulting SPR band overlaid with the SPR band from the Au—YSZ sample used for the previous NO$_2$ experiments is shown in FIG. 31. The SPR band from the 900° C. sample peaks at 570 nm and has a FWHM of 108 nm, as compared to a SPR band that peaks at 604 nm and has a FWHM of 170 nm. From the previous analysis of SPR bands and their comparison with particle sizing from XRD analysis, the 900° C. sample has an estimated Au particle diameter of about 10 nm as compared to the about 23 nm diameter particles used for the NO$_2$ studies. The control of the Au particle size is again achieved through the variation of the thermal annealing process as the larger nanoparticle sample was annealed at 1000° C. for 6 hours.

Figure 32:
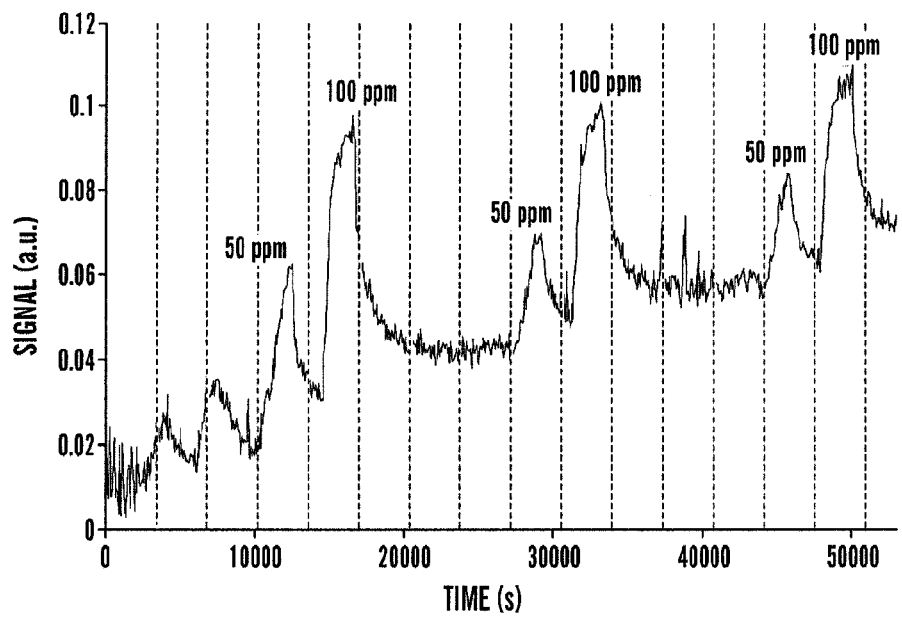
FIG. 32 is a graph of the sensing signal vs. time for $NO_2$ exposures on a 10 nm diameter gold nanoparticle sample.
Figure 33:
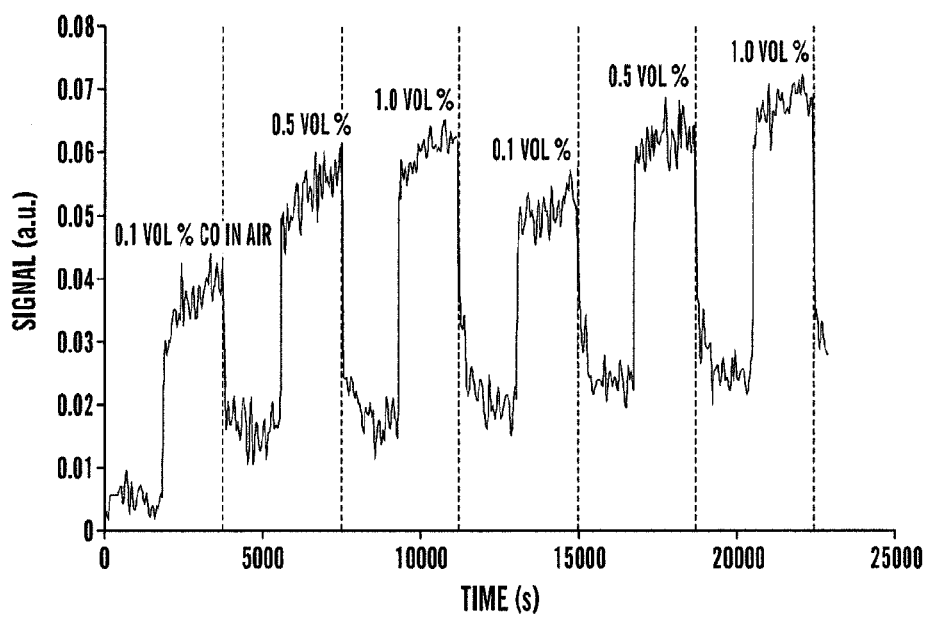
FIG. 33 is a graph of the CO sensing signal vs. time for CO exposures on a 10 nm diameter Au nanoparticle film.

Both NO$_2$ and CO exposure tests were performed with the 10 nm diameter sample as seen in FIGS. 32 and 33, respectively, which display the change in peak position as a function of time for a series of exposures. As can be seen in FIG. 32, for the NO$_2$ tests at 500° C., the change in peak position does not reliably respond nor recover well from the NO$_2$ exposures, and in fact the change in peak position never fully saturates within the 30 minute exposure window indicating that the response and recovery time of this sample towards NO$_2$ is much longer than for the 23 nm diameter sample previously used. FIG. 33 displays the change in peak position as a function of time for a series of CO exposures at 500° C. and as can be seen in this figure the peak position reversibly responds to the CO gas pulses, albeit with a smaller signal change than observed for the 19 nm Au NP diameter sample data shown in FIG. 14. While these initial results are interesting as it demonstrates that by changing the nanoparticle diameter, it is possible to modify the sensing characteristics of these films, a detailed study on the Au NP size dependent sensing properties of these Au—YSZ films is required to fully understand the CO, H$_2$ and NO$_2$ reaction dynamics. From this complete study optimized films would be developed for each of these target gases and a combination of these films used in a sensing array from which the individual sensing signals could be deconvoluted from each would be a more feasible prospect than through the analysis of a single film.

Hydrocarbon Detection—Ethanol at 500° C.

Another aspect of the present invention is directed to the detection of hydrocarbons such as ethanol at elevated temperatures. For example, ethanol vapors were picked up and mixed into the gas stream through the use of a bubbler pick-up source. Liquid ethanol was placed in a glass vessel and held at room temperature. The partial pressure of ethanol in this vessel and under these conditions is 70 torr, which when picked up by a volumetric flow, 20 sccm of air and mixed with a larger volumetric flow, 1980 sccm, leads to a concentration of ethanol that is equal to 900 ppm concentration in a total flow of 2000 sccm. By varying the volumetric split of flow through the bubbler we are able to deliver ethanol exposures of 150, 1500 and 5000 ppm for these experiments.

For example, upon reaction of the surface bound O$^-$ ion (or O$^{2-}$) and the ethanol molecule, the electron previously bound to the O$^-$ ion (or O$^{2-}$) is donated back to Au$^+$ (or Au$^{2+}$) thus neutralizing (or reducing the positive charge) on the Au nanoparticle and causing the "blue shift" and narrowing of the surface plasmon resonance band of the Au nanoparticle as follows, Note, ethanol is depicted as C$_2$H$_5$O in the following chemical reactions. While it is presumed that at least one hydrogen atom will be removed from the ethanol molecule upon reaction, it is not clear as to which hydrogen atom or atoms will be removed upon reaction:

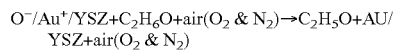

or alternatively,

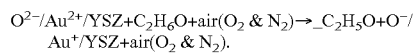

Figure 34:
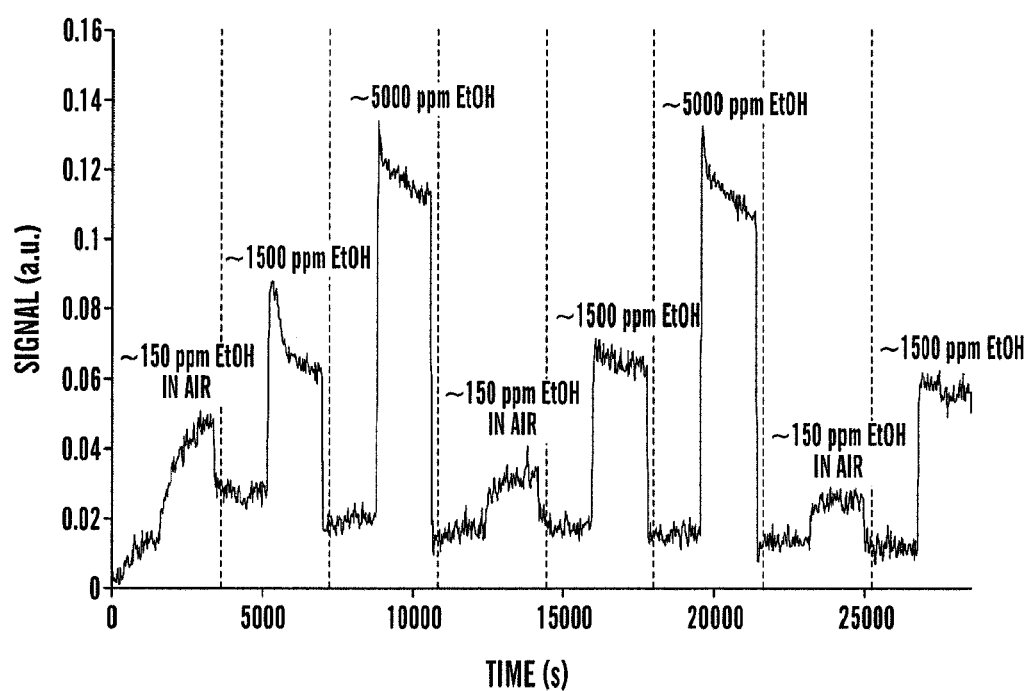
FIG. 34 is a graph of the ethanol sensing signal vs. time for ethanol exposures on the 10 nm diameter Au nanoparticle film.

FIG. 34 shows the sensing signal vs. time for these ethanol exposures and which illustrates the ability to reversibly detect ethanol under these conditions. As observed, the is an initial spike in the sensing signal upon activation of the ethanol gas pulse which is believed to be an artifact of the hydrocarbon gas source and delivery lines which in between gas pulses has a mild buildup of ethanol in the about 20 feet long ¼ inch tubing. Optimizing the hydrocarbon gas delivery lines may prevent this type of problem. Analysis of the change in the SPR band's peak position and FWHM indicate that the characteristic blue shift and narrowing of the SPR band upon reaction with O$^{2-}$, leading to electron donation back to the gold nanoparticles is the reaction mechanism for the detection of ethanol with these films.

Figure 35:
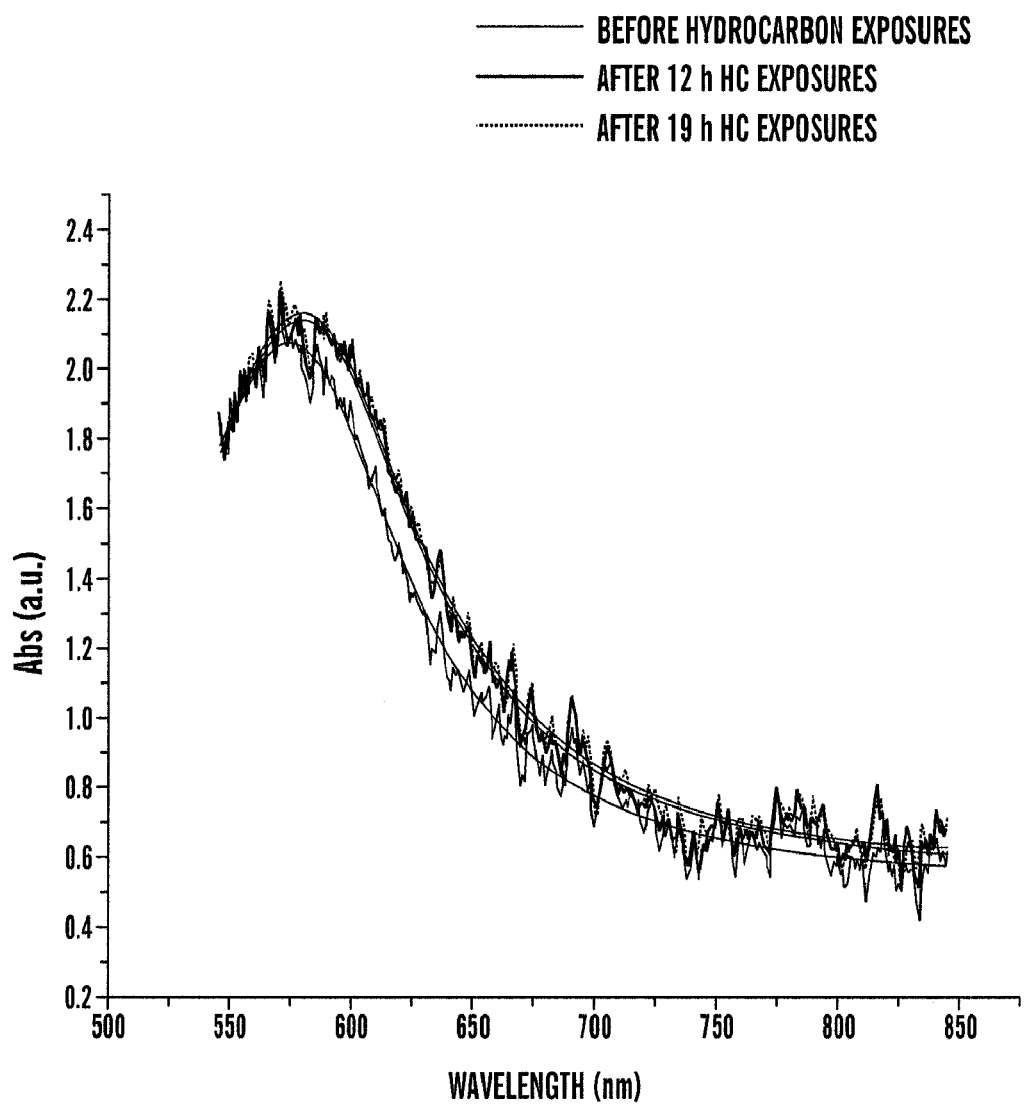
FIG. 35 is a graph of the SPR bands for the 10 nm diameter Au nanoparticle film before ethanol exposure and after 12 and 19 hours of ethanol sensing.

A total of 20 hours of ethanol exposure experiments have been performed resulting in the detection of 150 ppm of ethanol which as seen in the figures the sensing signal at 150 ppm has little noise leading to the belief that these Au—YSZ films can sense much lower ethanol concentrations and furthermore these films should be able to sensitively detect other hydrocarbons as well. However, of particular interest is that the Au—YSZ films appear to have no obvious problems with carbon buildup due to the catalytic reaction of ethanol which should produce CO$_2$ and water as the final by-products of this reaction (i.e., if the hydrocarbon molecule breaks down completely upon reaction with Au—YSZ). The initial conclusion is from analysis of the SPR band of the Au—YSZ sample prior to any ethanol exposure and then after 12 and then 19 hours of experiments. These three SPR bands are overlaid and displayed in FIG. 35. As can be seen, there is a change in the SPR band after the initial 12 hour experiment but then there is no measurable change in the SPR band after another 7 hours of experiments with ethanol concentrations of 150, 1500 and 5000 ppm in air at an operating temperature of 500° C. Materials analysis of the Au—YSZ film after much longer exposures, e.g., a month, may aid in determining the extent of carbon buildup, and particle size may also play a role in the detection of hydrocarbons, which may lead to optimizing hydrocarbon detection.

System

As described above, the present invention provides Au—YSZ nanocomposite films for the detection of CO, $NO_2$, $H_2$ and ethanol under harsh environment conditions. For CO, $H_2$ and ethanol there is a reaction with the $O^{2-}$ ions which occupy vacancies in the YSZ matrix which form an oxidized product with the electrons from the oxygen anion being donated back to the Au nanoparticles that induces the characteristic blue shift of the SPR band. The temperature and oxygen titration experiments confirm that for this reaction to take place, the operation temperature must be above the threshold required for formation of $O^{2-}$ from the background oxygen and if there is no background oxygen or the temperature is below this formation threshold the reaction is deactivated and sensing is not possible. Desirably, the operating temperature is above about 400° C. with about 500° C. being preferable. Likewise for CO and $H_2$, as long as the oxygen levels are above about 8% the reactions are independent of the oxygen concentration.

The $NO_2$ reaction proceeds through the catalytic reduction of $NO_2$ on hot gold surfaces to form NO and an O atom. The oxygen atom then forms an $O^{2-}$ ion thus removing electrons from the gold nanoparticle causing the characteristic redshift of the SPR band. For this reaction background oxygen actually reduces the signal contrast and by reducing these levels to 5 and 10 vol. % the sensing signal for $NO_2$ increases as there are more sites available for the formation of an $O^{2-}$ ion as the sample is not saturated from the background oxygen concentration. Therefore the detection of $NO_2$ is dependent on the background oxygen levels even between 5 and 20 vol. % oxygen and is also dependent on temperature as it does have to be above the threshold for $O^{2-}$ formation.

As described above, it appears that each of the reactions, CO, $H_2$ and $NO_2$ on Au—YSZ has a gold nanoparticle size dependence. Such dependence may allow sensing arrays to be designed with films that have a preference for reacting with a particular species. The detection limits for $NO_2$ observed were about 5 ppm in an air carrier gas and at 500° C., which is close to the 1 ppm desired for use in active sensing system on jet turbines. The detection limits for CO were not pushed strongly but at 1,000 ppm still showed strong signal changes implying that 100 ppm detection limits with these initial films is likely possible. For the $H_2$ detection concentrations as low as 500 ppm with strong signal to noise ratios imply a detection limit of about 250 ppm. Since the ethanol studies have only been preliminary, detection limits cannot be estimated, however the significant result from these studies is that they did not appear to become poisoned with carbon within the 20 hours of run time thus performed. Furthermore, all of the films used for this study have shown to be quite rugged and within the lifetime of this study have not shown any significant degradation with time or chemical exposure. Therefore in conclusion it appears that the all-optical detection of CO, $H_2$, $NO_2$ and hydrocarbons using the optical signature of Au nanoparticles embedded in a YSZ matrix has shown strong promise for use as a harsh environment compatible chemical sensor.

For environments where there is only one constituent present (e.g., CO, $NO_2$, $H_2$ or hydrocarbons) in the gas containing oxygen or in a gas such as air, a single sensing film may be employed to detect the constituent and/or the concentration thereof. For example, a single sensing film may be used in turbine engines where the CO and unburnt fuel levels are low (ppb levels) such that they will not interfere with the measurement, but the $NO_2$ is high (about 100 ppm). As described above, the present invention allows detection of $NO_2$ at 5 ppm.

Cross-Sensitivity

Due to cross sensitivity, for example where a gas has more than one constituent such as a mixture of CO, $NO_2$, hydrogen, and hydrocarbons, for detecting with one sensing film, each constituent may contribute to a resulting signal. For example, CO and hydrogen induce a similar signal, e.g., blue shift, while $NO_2$ will induce a red shift.

For example, as discussed above, a sensing film tailored for hydrogen will show a strong response for 1% hydrogen as shown in FIG. 21 compared to the weak response when using the film to detect 1% CO as shown in FIG. 20, i.e., the hydrogen sensing at 1% hydrogen being a factor of 6 better that the CO sending of CO at 1%. In this case, the Au particle size being 19 nanometers. Where a smaller particle size of Au is used, the response for CO is better as discussed above.

Another aspect of the present invention is directed to the use of an array of nanocomposite materials containing Au nanoparticles, with each element of the array tailored for the optimized detection of the target gas of interest. By interpreting the sensing signals from each array element within the sensing array, a "fingerprint-like" signature of the target gas may be obtained for a more accurate and reliable detection of the target gas of interest within a background of other chemical species. Tailoring of the array elements will include the variation of the nanoparticle size, percent content within the film, film thickness, and matrix type.

Figure 36:
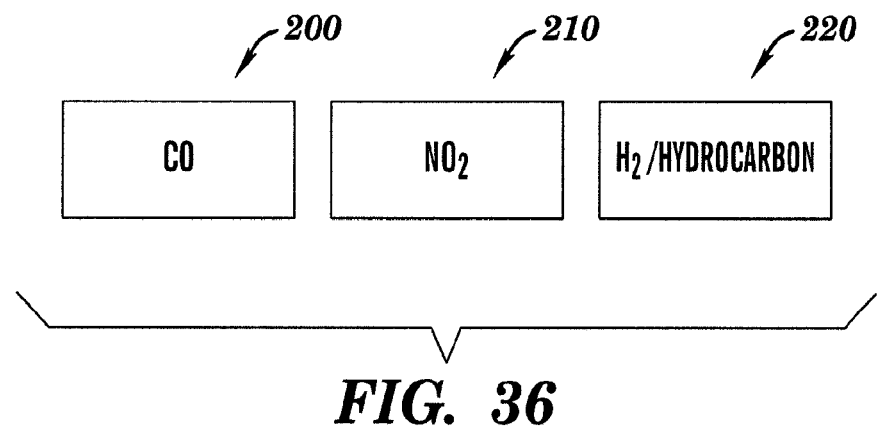
FIG. 36 is another embodiment of a plurality of optical sensors in accordance with the present invention.

FIG. 36 illustrates a plurality of sensor films such as three sensing films to better distinguish the signature of various constituents in a gas containing oxygen as described above. The three separate tailored sensors may include a CO sensor 200, a $NO_2$ sensor 210, and a hydrogen or hydrocarbon sensor 220. For example, the CO sensing film is optimized for the detection of carbon monoxide, the $NO_2$ sensing film is optimized for nitrogen dioxide, and the $H_2$/hydrocarbon is optimized for hydrogen or hydrocarbons. Desirably, for power generation turbines burning a fuel such as methane, natural gas, or jet engines burning jet fuel, a combination CO sensor, a $NO_2$ sensor, and hydrocarbon sensor may be employed.

Figure 37:
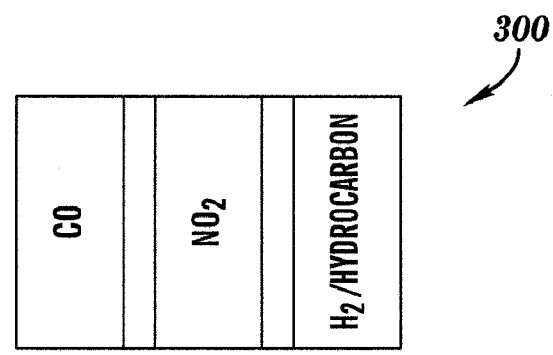
FIG. 37 is another embodiment of an optical sensor in accordance with the present invention.
Figure 38:
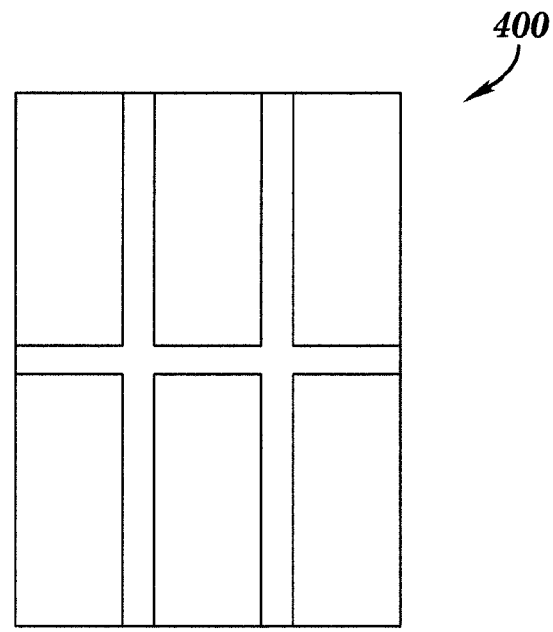
FIG. 38 is another embodiment of an optical sensor in accordance with the present invention.

FIG. 37 illustrates a three element or film array 300 formed on the same substrate and tailored and operable as described above. FIG. 38 illustrates a six-element array 400 providing multiple sensing capabilities and/or redundant sensors as described above.

By looking at the signals from the plurality of different sensing films or elements, a pattern is observed and comparing the signals or pattern to a database or known concentrations of the three constituents, it is possible to identify the constituents and the amounts of concentration.

With reference again to FIGS. 5 and 6, different types of gases may be detected by employing one or more filters disposed adjacent the detector to aid in filtering out light and allowing a particular wavelength to be detected. For example, a blue interference bandpass filter (which preferentially transmits the blue portion of the SPR absorption spectrum) may be used for detection of CO, and a red interference bandpass filter (which preferentially transmits the red portion of the SPR absorption spectrum) may be used for the detection of $NO_2$.

Figure 39:
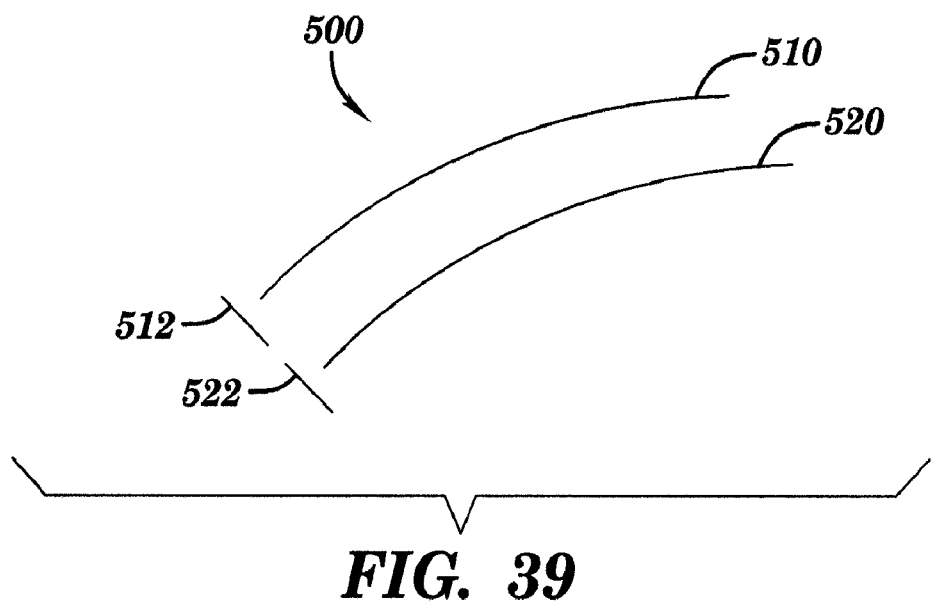
FIG. 39 is another embodiment of an optical gas sensor in accordance with the present invention.

FIG. 39 illustrates another embodiment of an optical sensor 500 in accordance with the present invention, which generally employs two optical fibers, each with a specific film for sensing either CO or $NO_2$. For example, the optical sensor may include a first optical fiber 510 coated with thin film comprising Au—YSZ for detecting CO and a second optical fiber 520 coated with thin film which includes Au—YSZ for detecting $NO_2$, as a function of the spectral shift and tailoring described above. Suitable filters 512 and 522 may also be employed to select out the specific wavelength of light for analysis.

Figure 40:
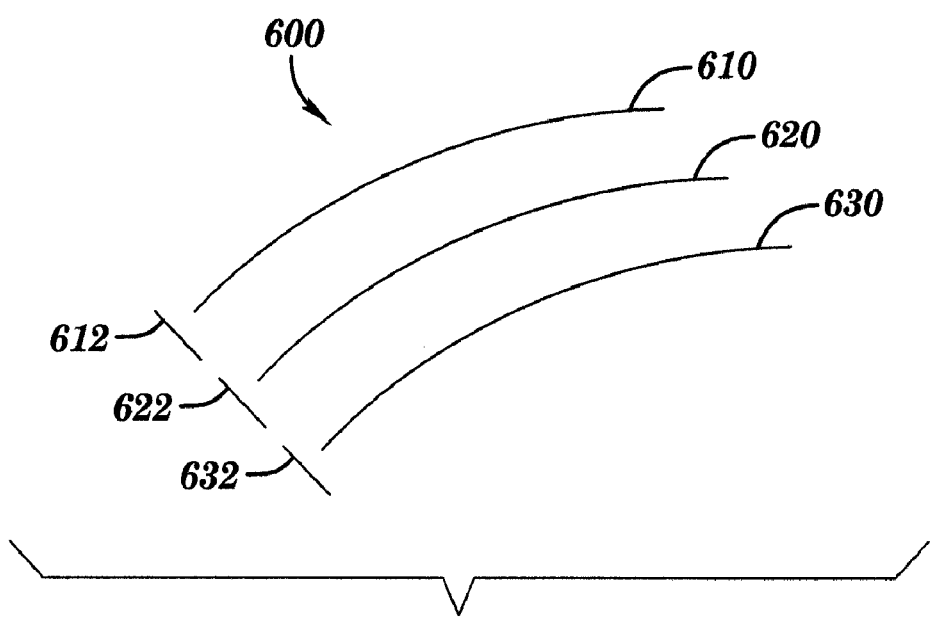
FIG. 40 is another embodiment of an optical gas sensor in accordance with the present invention.

FIG. 40 illustrates another embodiment of an optical sensor 600 in accordance with the present invention, which generally employs three optical fibers, each with a specific film for sensing either CO, $NO_2$, and $H_2$ or hydrocarbons. For example, the optical sensor may include a first optical fiber 610 coated with thin film comprising Au—YSZ for detecting CO, a second optical fiber 620 coated with thin film which includes Au—YSZ for detecting $NO_2$, and a third optical fiber 630 coated with thin film which includes Au—YSZ for detecting $H_2$ or hydrocarbons, as a function of the spectral shift and tailoring described above. Suitable filters 612, 622, and 632 may also be employed to select out the specific wavelength of light for analysis.

For these embodiments, the gas sensing system may include suitable lights sources, detectors, microcontrollers or processors, input/output devices, and storage devices as described above.

Figure 41:
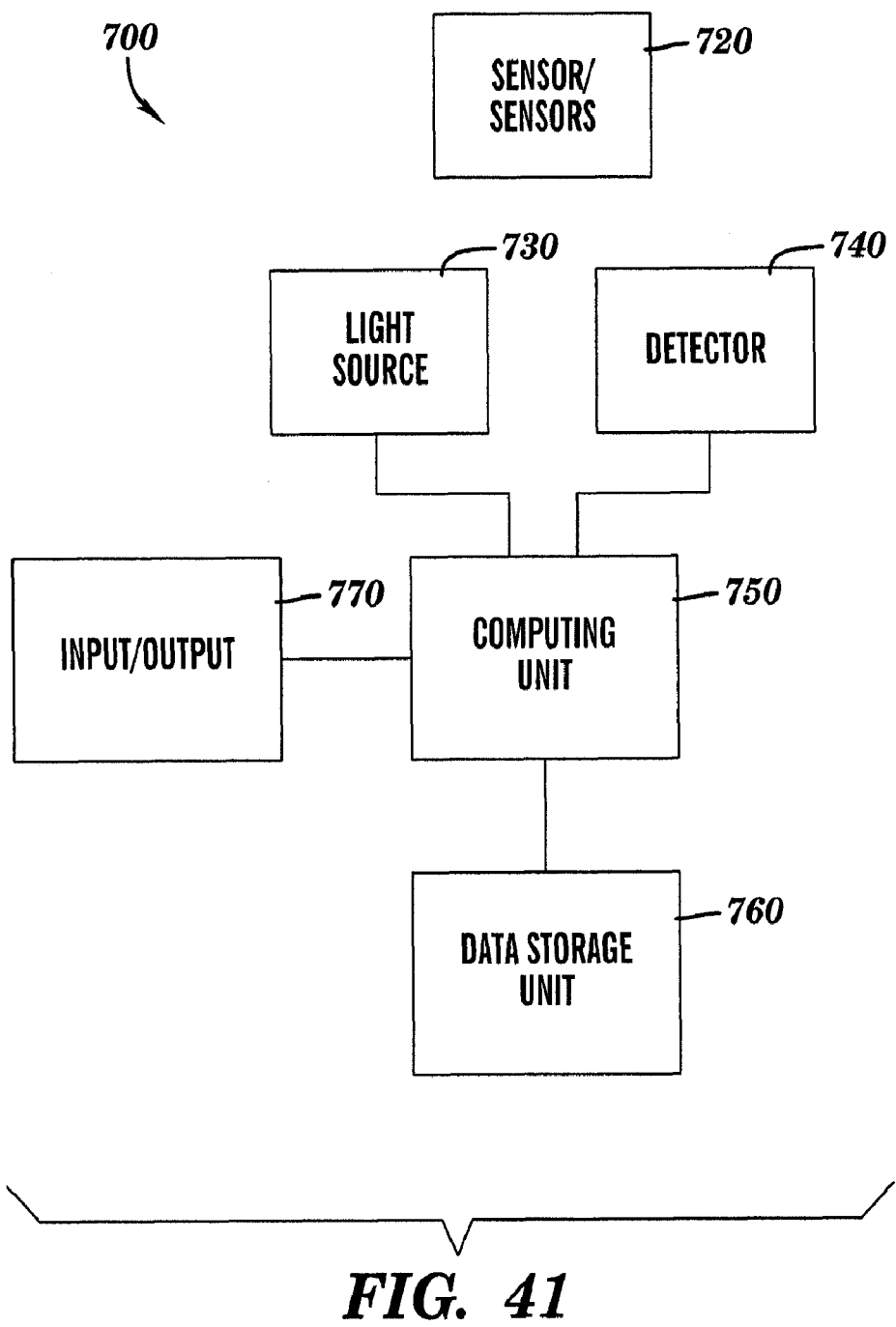
FIG. 41 is an optical gas sensor system in accordance with the present invention.

For example, with reference to FIG. 41, therein illustrated is a gas sensing system 700 in accordance with the present invention for detecting one or more constituents in a gas containing oxygen. The system may include a sensing material or plurality of sensing materials 720 having a metal embedded in a catalytically active matrix, a light source 730 for directing light on to said sensing material, a light detector 740 for detecting light reflected from the sensing material, a processor 750 operable to detect the constituent in the gas by a change in the absorption spectrum of the sensing material due to the exposure of the sensing material to the constituent in the gas at the temperature which causes a chemical reaction in the sensing material compared to the absorption spectrum of the sensing material in the absence of the constituent in the gas. Desirably, the system may include a data storage 760 unit having database of a plurality of absorption spectrum changes for comparison to the detected absorption spectrum. One or more suitable input/output devices 770 may also be provided.

Other suitable catalytically active matrices may include titanium (IV) oxide or titanium dioxide ($TiO_2$).

Upon sulfur containing gases or CO binding to the nanoparticle the SPR band will characteristically shift in wavelength and intensity. With regard to solid oxide fuel cells, the nanocomposite material may be designed to be the weak link and thus serve as a first responder to the event of a sulfur containing gas or CO break through. A feedback loop data system may read the signal from the "weak link" sensor and either perform a system shutdown or activate a method of reactivating the sulfur containing gas or CO catalytic reforming traps within the SOFC system to prevent massive contamination and breakdown of the solid oxide fuel cell system.

An all-optical sensing device is intrinsically safe with respect to explosion hazards and would allow for the remote sensing of harsh environments. Use of an array of nanoparticle nanocomposite materials interrogated with either a single optical source and detector or individual sources and detectors allows for the interpretation of the chemical "fingerprint" of the gas mixture and the selective and sensitive identification and analysis of gas mixtures containing hydrogen, $NO_x$, CO, $O_2$, hydrocarbons (unburnt fuel) water and sulfur containing gases.

From the present description, it will be appreciated by those skilled in the art that instead of above-noted filters and detectors, a spectrometer (or other light dispersing device) coupled to a detector may be employed in accordance with the present invention.

While various embodiments of the present invention have been illustrated and described, it will be appreciated by those skilled in the art that many further changes and modifications may be made thereunto without departing from the spirit and scope of the invention.

The invention claimed is:

1. A method for detecting a constituent in a gas containing oxygen, the method comprising:
   providing a sensing material comprising a metal embedded in a catalytically active matrix;
   exposing the sensing material and the constituent in the gas to a temperature above about 400° C.;
   projecting light onto the sensing material; and
   detecting the constituent in the gas by a change in the absorption spectrum of the metal due to the exposure of the sensing material to the constituent in the gas at the temperature which causes a chemical reaction in the sensing material compared to the absorption spectrum of the metal in the absence of the constituent in the gas.

2. The method of claim 1 further comprising detecting comprises determining a concentration of the constituent in the gas based on an amount of the change in the absorption spectrum.

3. The method of claim 1 wherein the detecting comprises subtracting the absorption spectrum of the sensing metal in the gas from the absorption spectrum of the metal in the gas containing the constituent, determining the peak to peak difference therebetween, and determining a concentration of the constituent in the gas based on the amount of the peak to peak difference.

4. The method of claim 1 further comprising comparing the change in the absorption spectrum to a database of absorption spectrum changes.

5. The method of claim 1 wherein the detecting comprises detecting a "blue shift" to shorter wavelengths in the absorption spectrum.

6. The method of claim 1 wherein the detecting comprises detecting carbon monoxide in the gas.

7. The method of claim 1 wherein the detecting comprises detecting hydrogen in the gas.

8. The method of claim 1 wherein the detecting comprises detecting hydrocarbon in the gas.

9. The method of claim 1 wherein the detecting comprises detecting a "redshift" to longer wavelengths in the absorption spectrum.

10. The method of claim 1 wherein the detecting comprises detecting nitrogen dioxide in the gas.

11. The method of claim 1 wherein the metal comprises gold and the catalytically active matrix comprises a yttria stabilized zirconia matrix.

12. The method of claim 1 wherein the providing comprises providing the sensing material annealed at about 900° C.

13. The method of claim 1 wherein the exposing the sensing material and the constituent in the gas comprises exposing the sensing material and the constituent in the gas to a temperatures between about 500° C. to about 800° C.

14. The method of claim 1 wherein the detecting further comprises filtering the light to permit identification of a wavelength of the absorption spectrum of the sensing metal.

15. The method of claim 1 wherein the providing the sensing material comprises providing the sensing material having a grain size of the metal about equal to the grain size of the catalytically active matrix.

16. The method of claim 1 wherein the providing the sensing material comprises providing the sensing material having a grain size of the metal and the grain size of the catalytically active matrix of about 19 nanometers.

17. The method of claim 1 wherein the providing the sensing material comprises providing the sensing material on a sapphire substrate.

18. The method of claim 1 wherein the providing the sensing material comprises providing the sensing material on an optical fiber.

19. A method for detecting a plurality of constituents in a gas containing oxygen, the method comprising:
provide a plurality of sensing materials comprising a metal embedded in a catalytically active matrix;
exposing the plurality of sensing materials and the plurality of constituents in the gas to a temperature above about 400° C.;
projecting light onto the sensing materials; and
detecting the constituents in the gas by a change in the absorption spectrum of the metal in the plurality of sensing materials due to the exposure of the plurality of sensing materials to the constituents in the gas at the temperature which causes a chemical reaction in the plurality of sensing materials compared to the absorption spectrum of the metal in the plurality of sensing materials in the absence of the constituents in the gas.

20. The method of claim 19 further comprising tailoring each of the plurality of sensing materials to a different one of the plurality of constituents.

21. The method of claim 19 further comprising tailoring each of the plurality of sensing materials to a different one of the plurality of constituents by varying the grain size of the metal in the catalytically active matrix.

22. A system for detecting a constituent in a gas containing oxygen, said system comprising:
a sensing material comprising a metal embedded in a catalytically active matrix;
a light source for directing light on to said sensing material;
a light detector for detecting light reflected from the sensing material; and
a processor operable to detect the constituent in the gas by a change in the absorption spectrum of the metal due to the exposure of the sensing material to the constituent in the gas at the temperature which causes a chemical reaction in the sensing material compared to the absorption spectrum of the metal in the absence of the constituent in the gas.

23. The system of claim 22 wherein said processor is operable to determine a concentration of the constituent in the gas based on an amount of the change in the absorption spectrum.

24. The system of claim 22 wherein said processor is operable to subtract the absorption spectrum of the metal in the gas from the absorption spectrum of the metal in the gas containing the constituent, determine the peak to peak difference therebetween, and determine a concentration of the constituent in the gas based on the amount of the peak to peak difference.

25. The system of claim 22 wherein said processor is operable to compare the change in the absorption spectrum to a database of absorption spectrum changes.

26. The system of claim 22 wherein said processor is operable to detect a "blue shift" to shorter wavelengths in the absorption spectrum.

27. The system of claim 22 wherein said processor is operable to detect carbon monoxide in the gas.

28. The system of claim 22 wherein said processor is operable to detect hydrogen in the gas.

29. The system of claim 22 wherein said processor is operable to detect hydrocarbon in the gas.

30. The system of claim 22 wherein said processor is operable to detect a "redshift" to longer wavelengths in the absorption spectrum.

31. The system of claim 22 wherein said processor is operable to detect nitrogen dioxide in the gas.

32. The system of claim 22 wherein the metal comprises gold and the catalytically active matrix comprises a yttria stabilized zirconia matrix.

33. The system of claim 22 wherein the sensing material is annealed at about 900° C.

34. The system of claim 22 further comprising a filter for filtering the light to permit identification of a wavelength of the absorption spectrum of the metal.

35. The system of claim 22 wherein the sensing material comprises a grain size of the metal about equal to the grain size of the catalytically active matrix.

36. The system of claim 22 wherein the sensing material comprises a grain size of the metal and the grain size of the catalytically active matrix of about 19 nanometers.

37. The system of claim 22 wherein the sensing material is disposed on a sapphire substrate.

38. The system of claim 22 wherein the sensing material is disposed on an optical fiber.

39. A system for detecting a plurality of constituents in a gas containing oxygen, the system comprising:
a plurality of sensing materials comprising a metal embedded in a catalytically active matrix;
a light source for directing light onto said plurality of sensing materials;
a light detector for detecting light reflected from said plurality of sensing materials; and
a processor operable to detect the plurality of constituents in the gas by a change in the absorption spectrum of the metal in the plurality of sensing materials due to the exposure of said plurality of sensing materials to the plurality of constituents in the gas at the temperature which causes a chemical reaction in the plurality of sensing materials compared to the absorption spectrum of the metal in the plurality of sensing materials in the absence of the constituents in the gas.

40. The system of claim 39 further comprising tailoring each of the plurality of sensing materials to a different one of the plurality of constituents to optimize the change in the absorption spectrum for a particular constituent.

41. The system of claim 40 wherein each of the plurality of sensing materials comprises a metal having a different grain size.

42. The system of claim 40 wherein said processor is operable to compare the change in the plurality of absorption spectrums to a database of a plurality of absorption spectrum changes.

* * * * *